United States Patent [19]
Gross

[11] Patent Number: 6,099,857
[45] Date of Patent: Aug. 8, 2000

[54] CELL MEMBRANE FUSION COMPOSITION AND METHOD

[75] Inventor: Richard W. Gross, St. Louis, Mo.

[73] Assignee: Washington University, St. Louis, Mo.

[21] Appl. No.: 09/092,617

[22] Filed: Jun. 5, 1998

Related U.S. Application Data

[62] Division of application No. 08/511,903, Aug. 7, 1995, Pat. No. 5,766,626, which is a continuation of application No. PCT/US95/06056, May 15, 1995, abandoned, which is a continuation-in-part of application No. 08/243,645, May 16, 1994, abandoned.

[51] Int. Cl.$^7$ .......................... A61K 9/127; A61K 9/133
[52] U.S. Cl. .......................... 424/450; 424/94.3; 935/54
[58] Field of Search .......................... 426/450; 436/829; 424/1.21, 9.321, 4.51, 417, 94.3; 935/54

[56] References Cited

U.S. PATENT DOCUMENTS

| | | |
|---|---|---|
| 3,869,482 | 3/1975 | Wolfe . |
| 5,208,036 | 5/1993 | Eppstein et al. . |
| 5,264,618 | 11/1993 | Felgner et al. . |
| 5,302,706 | 4/1994 | Smith . |

OTHER PUBLICATIONS

Allen, T.M., et al., "Membrane Contact, Fusion, and Hexagonal ($H_{II}$) Transitions in Phosphatidylethanolamine Liposomes," *Biochem.* 29:2976 (1990).

Almers, W., and Tse, F.W., "Transmitter Release from Synapses: Does a Preassembled Fusion Pore Initiate Exocytosos?" *Neuron* 4:813 (1990).

Bentz, J., et al., "Destabilization of Phosphatidylethanolamine–Containing Liposomes: Hexagonal Phase and Asymmetric Membranes," *Biochemistry* 26:2105 (1987).

Bentz, J., and Ellens, H., "Membrane Fusion: Kinetics and Mechanisms," *Colloids & Surfaces* 30:65 (1988).

Blank, M.L., and Snyder, F., "Improved High–Performance Liquid Chromatographic Method for Isolation of Platelet–Activating Factor from other Phospholipids," *J. Chromatograpy* 273:415 (1983).

Bligh, E.G., and Dyer, W.J., "A Rapid Method of Total Lipid Extraction and Purification," *Canadian J. Biochemi. & Physiol.* 37(8):911 (1959).

Breckenridge, W.C., et al., "Adult Rat Brain Synaptic Vesicles—Lipid Composition," *Biochim. Biophys. Acta* 320:681 (1973).

Chen, X., and Gross, R., "Phospholipid Subclass–Specific Alterations in the Kinetics of Ion Transport Across Biologic Membranes," *Biochem.* 33:13769 (1994).

Chernomordik, L.V., et al., "Lysolipids Reversibly Inhibit $Ca^{2+}-$, GTP– and pH–Dependent Fusion of Biologicl Membranes," *FEBS* 318(1):71 (1993).

Cullis, P.R., and de Kruijff, B., "Lipid Polymorphism and the Functional Roles of Lipids in Biological Membranes," *Biochim. Biophys. Acta* 559:399 (1979).

Cullis, P.R., and Hope, M.J., "Physical Properties and Functional Roles of Lipids in Membranes," in *Biochemistry of Lipids, Lipoproteins and Membranes* (Vance, J., and Vance, D.E., Eds.) Elsevier Science Publishers B.V., The Netherlands, pp. 1–41 (1991).

Diaz, R., et al., "Vesicle Fusion Following Receptor–Mediated Endocytosis Requires a Protein Active in Golgi Transport," *Nature* 339:398 (1989).

(List continued on next page.)

Primary Examiner—Gollamudi S. Kishore
Attorney, Agent, or Firm—Peter J. Dehlinger; Judy M. Mohr; Iota Pi Law Group

[57] ABSTRACT

A lipid vesicle composition for use in delivering a vesicle-encapsulated agent to a target cell is disclosed. The composition is formed of vesicle-forming lipids, including at least 10 mole percent plasmalogen phospholipid with a small-volume polar head group. The composition may also include a fusion protein for promoting fusion of the vesicles to the target cells. A novel fusion protein identified as an isoform of glyceraldehyde-3-phosphate dehydrogenase is also disclosed.

12 Claims, 9 Drawing Sheets

OTHER PUBLICATIONS

Düzgünes, N., et al., "Lipid Mixing During Membrane Aggregation and Fusion: Why Fusion Assays Disagree," *Biochem.* 26:8435 (1987).

Düzgünes, N., "Membrane Fusion", in *Subcellular Biochemistry*, vol. 11 (Roodyn, D.B., Ed.) Plenum Press, New York, NY, pp. 195 (1985).

Ellens, H., et al., "Destabilization of Phosphatidylethanolamine Liposomes at the Hexagonal Phase Transition Temperature," *Biochem.* 25(2):285 (1986).

Ellens, H., et al., "Membrane Fusion and Inverted Phases," *Biochem.* 28:3692 (1989).

Fraley, R., et al., "Studies on the Mechanism of Membrane Fusion: Role of Phosphate in Promoting Calcium Ion Induced Fusion of Phospholipid Vesicles," *Biochem.* 19:6021 (1980).

Geurts van Kessel, W.S.M., et al., "High Performance Liquid Chromatographic Separation and Direct Ultraviolet Detection of Phospholipids," *Biochim. Biophys. Acta* 486:524 (1977).

Gross, R.W., "High Plasmalogen and Arachidonic Acid Content of Canine Myocardian Sarcolemma: A Fast Atom Bombardment Mass Spectroscopic and Gas Chromatography—Mass Spectroscopic Characterization," *Biochem.* 23:158 (1984).

Han, X., and Gross, R.W., "Plasmenylcholine and Phosphatidylcholine Membrane Bilayers Possess Distinct Conformational Motifs," *Biochem.* 29:4992 (1990).

Han, X., and Gross, R.W., "Nonmonotonic Alterations in the Fluorescence Anisotropy of Polar Head Group Labeled Fluorophores During the Lamellar to Hexagonal Phase Transition of Phospholipids," *Biophys. J.* 63:309 (1992).

Han, X., et al., "Semisynthesis and Purification of Homogeneous Plasmenylcholine Molecular Species," *Analyt. Biochem.* 200:119 (1992).

Hoekstra, D., "Role of Lipid Phase Separations and Membrane Hydration in Phospholiped Vesicle Fusion," *Biochem.* 21:2833 (1982).

Hoekstra, et al., "Fluorescence Method for Measuring the Kinetics of Fusion Between Biological Membranes," *Biochem.* 23:5675 (1984).

Leckband, D.E., et al., "Role of Calcium in the Adhesion and Fusion of Bilayers," *Biochem.* 32:1127 (1993).

Lohner, K., et al., "Phase Behavior of Ethanolamine Plasmalogen," *Chem. and Phys. of Lipids* 34:163 (1984).

Meers, P., et al., "Free Fatty Acid Enhancement of Catio–Induced Fusion of Liposomes: Synergism with Synexin and Other Promoters of Vesicle Aggregation," *Biochem.* 27:6784 (1988).

Nir, S., et al., "Mass Action Kinetics of Phosphatidylserine Vesicle Fusion as Monitored by Coalescence of Internal Vesicle Volumes," *Biochem.* 19:6030 (1980).

Papahadjopoulos, D., et al., "Cochleate Lipid Cylinders: Formation by Fusion of Unilamellar Lipid Vesicles," *Biochim. Biophys. Acta* 394:483 (1975).

Papahadjopoulos, D., et al., "Molecular Mechanisms of Calcium–Induced Membrane Fusion," *J. Bioenergetics and Biomembranes* 22(2):157 (1990).

Pollard, H.B., et al., "Synexin (Annexin VII) and Membrane Fusion During the Process of Exocytotic Secretion," in *Progress in Brain Research* (Joosse, J., et al., Eds.) Elsevier Science Publishers, The Netherlands, pp. 247–255 (1992).

Poste, G., and Allison, A.C., "Membrane Fusion," *Biochim. Biophys. Acta* 300:421 (1973).

Rupert, L.A.M., et al., "Calcium–Induced Fusion of Didodecylphosphate Vesicles: The Lamellar to Hexagonal II ($H_{II}$) Phase Transition," *J. Membrane Biol.* 95:255 (1987).

Siegel, D.P., et al., "Physiological Levels of Diacylglycerols in Phospholipid Membranes Induce Membrane Fusion and Stabilize Inverted Phases," *Biochem.* 28:3703–3709 (1989).

Söllner, T., et al., "Snap Receptors Implicated in Vesicle Targeting and Fusion," *Nature* 362:318 (1993).

Stamnes, M.A., and Rothman, J.E., "The Binding of AP–1 Clathrin Adaptor Particles to Golgi Membranes Requires ADP–Ribosylation Factor, a Small GTP–Binding Protein," *Cell* 73:999 (1993).

Struck, D.K., et al., "Use of Resonance Energy Transfer to Monitor Membrane Fusion," *Biochem.* 20:4093 (1981).

Sundler, R., and Papahadjopoulos, D., "Control of Membrane Fusion by Phospholid Head Groups—Phosphatidate/Phosphatidyllinositol Specificity," *Biochim. Biophys. Acta* 649:743 (1981).

Verkleij, A.J., "Lipidic Intramembranous Particles," *Biochim. Biophys. Acta* 779:43 (1984).

Vogel, S.S., et al., "Lysophosphatidylcholine Reversibly Arrests Exocytosis and Viral Fusion at a Stage Between Triggering and Membrane Merger," *J. Biol. Chem.* 268(4):25764 (1993).

von Wedel, R.J., et al., "Transfer of Synaptic Vesicle Antigens to the Presynaptic Plasma Membrane During Exocytosis," *Proc. Natl. Acad. Sci. USA* 78(2):1014 (1981).

Wilschut, J., and Papahadjopoulos, D., "$Ca^{2+}$–Induced Fusion of Phsopholipid Vesicles Monitored by Mixing of Aqueous Contents," *Nature* 281:590 (1979).

Wilschut, J., et al., "Studies on the Mechanism of Membrane Fusion: Kinetics of Calcium Ion Induced Fusion of Phosphatidylserine Vesicles Followed by a New Assay for Mixing of Aqueous Vesicle Contents," *Biochem.* 19:6011 (1980).

Wilschut, J., and Hoekstra, K., "Membrane Fusion: Lipid Vesicles as a Model System," *Chemistry and Physics of Lipids* 40:145 (1986).

Westhead, E.W., "Lipid Composition and Orientation in Secretory Vesicles," *Ann. NY Acad. Sci.* 493:92 (1987).

Wilson, D.W., et al., "Intracellular Membrane Fusion," *TIBS* 16:334 (1991).

Yeagle, P.L., "Lipid Regulation of Cell Membrane Structure and Function," *FASEB J.* 3:1834 (1989).

Zimmerberg, J., et al., "Mechanisms of Membrane Fusion," *Annu. Rev. Biophys. Biomol. Struct.* 22:443–466 (1993).

Hope in BBRC 110, #1, pp. 15–22, 1983.

Hug in BBA 1097, pp. 1–17, 1991.

Fig. 8A
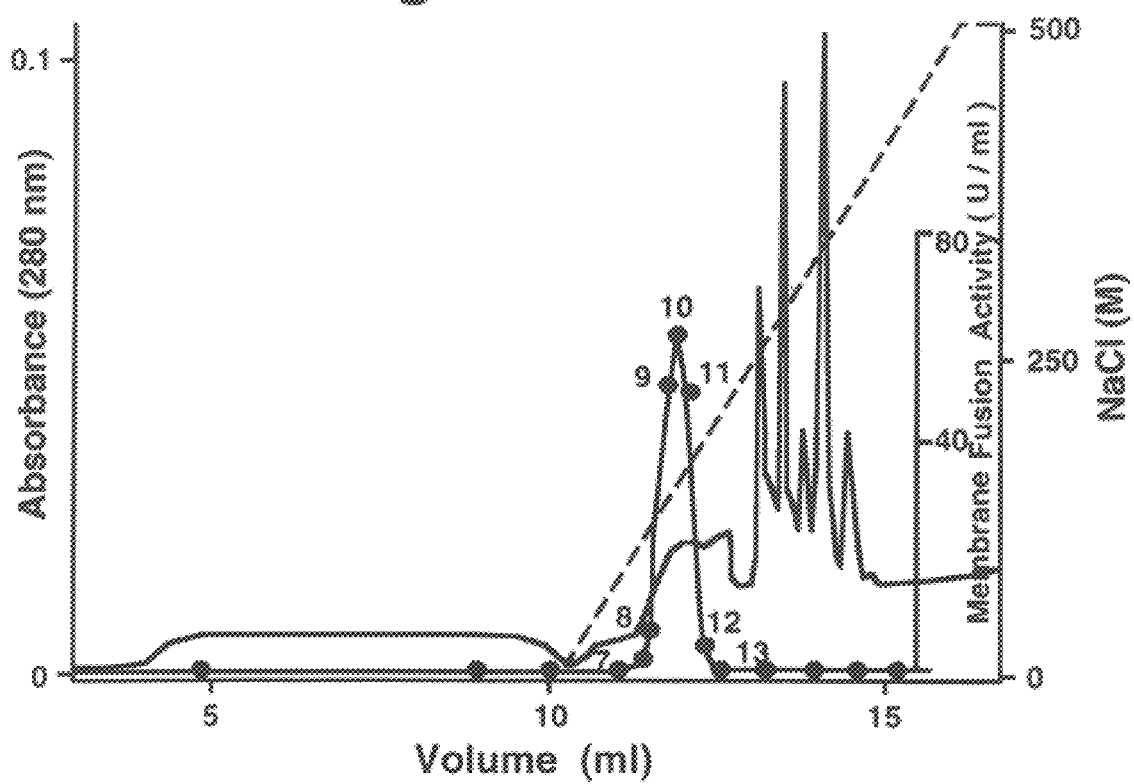
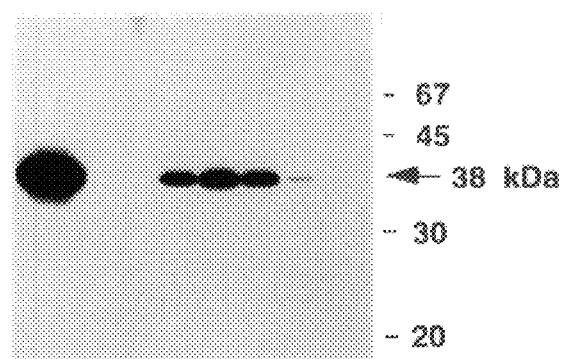
Fig. 8B

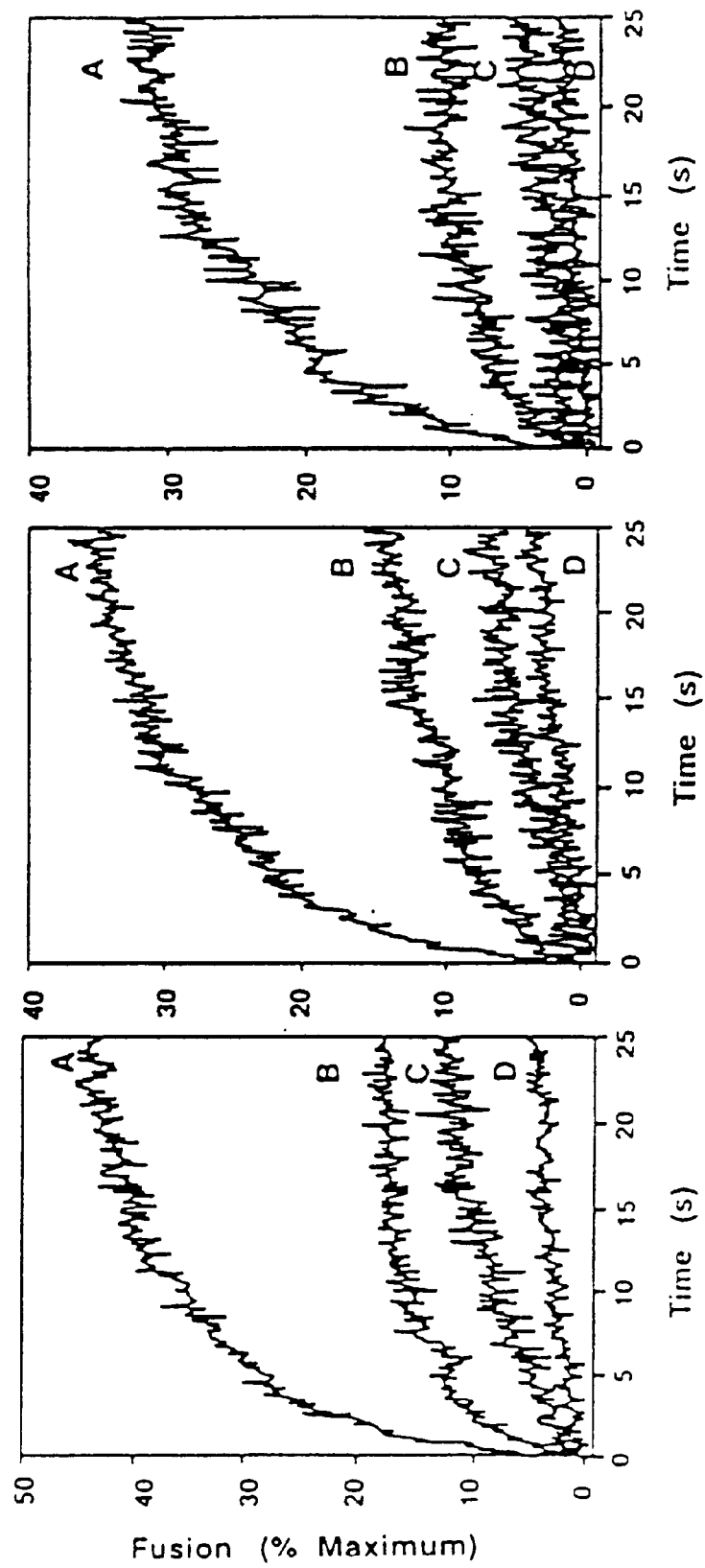

CELL MEMBRANE FUSION COMPOSITION AND METHOD

The present application is a divisional application of application Ser. No. 08/511,903, filed Aug. 7, 1995, now U.S. Pat. No. 5,766,626, which is a continuation of PCT US95/06056, filed May 15, 1995, now abandoned, which is a continuation-in-part of U.S. application Ser. No. 08/243,645, filed May 16, 1994, now abandoned.

Portions of this invention were supported by Grant No. 34839 from the National Institutes of Health. The government has certain rights in this invention.

FIELD OF THE INVENTION

The present invention relates to fusogenic lipid vesicles, and to the use of such vesicles, e.g., for drug delivery.

REFERENCES

Arcari, P., et al., *Biochemical Genetics* 27:439–450 (1989).

Bental, M., et al., *Biochim. Biophys. Acta* 898:239–247 (1987).

Blank and Snyder, *J. Chromatogr.* 273:415–420 (1983).

Bligh, E. G., and Dyer, W. J., Can. *J. Biochem. Phys.* 37:911–917 (1959).

Blobel, C. P., et al., *Nature* 356(6366):248–252 (1992).

Cori, G. T., et al., *J. Biol. Chem.* 173:605–618 (1948).

Cullis, P. R., and Hope, M. J., in BIOCHEMISTRY OF LIPIDS, LIPOPROTEINS, AND MEMBRANES, Elsevier Science Publishers, New York, N.Y. (1991).

Düzgünes, N. A., et al., *Biochemistry* 26:8435–8552 (1987).

Edwardson, J. M., et al., *FEBS Lett.* 320(1):52–56 (1993).

Epand, R. M., et al., *Biopolymers* 32(4):309–314 (1992).

Fredericksen, B. L., and Whitt, M. A., *J. Virol.* 69(3):1435–1443 (1995).

Geurts van Kessel, et al., *Biochem. Biophys. Acta.* 486:524–30 (1977).

Glaser, P. E., and Gross, R. W., *Biochemistry* 33:5805–5812 (1994).

Gross, R. W., *Biochemistry* 23:158–165 (1984).

Han, X., and Gross, R. W., *Biochemistry* 29:4992–4996 (1990).

Han, X., and Gross, R. W., *Biophys. J.* 63:309–316 (1992).

Han, X., et al., *Analyt. Biochem.* 200:119–124 (1992).

Harlow, E., and Lane, D., in ANTIBODIES: A LABORATORY MANUAL, Cold Spring Harbor Laboratories, Cold Spring Harbor, N.Y. (1988).

Hazen, S. L., et al., *J. Biol. Chem.* 265:10622–10630 (1990).

Hoekstra, *Biochemistry* 21:283–2840 (1982).

Hoekstra, D., et al., *Biochemistry* 23:5675–5681 (1984).

Ito, Y., et al., *J. Virol.* 66(10):5999–6007 (1992).

Morrison, T., et al., *J. Virol.* 65(2):813–822 (1991).

Rapaport, D., and Shai, Y., *J. Biol. Chem.* 269(21):15124–31 (1994).

Sakai, K., et al., *Biochim. Biophys. Acta* 1077:192–196 (1991).

Shelanski, M. L., et al, *Proc Nat Acad Sci, USA*, 70:765 (1973).

Stamatatos, L., and Silvius, J. R., *Biochim. Biophys. Acta* 905:81–90 (1987).

Stamnes, M. A., and Rothman, J. E., *Cell* 73:999–1005 (1993).

Steck, T. L., and Kant, J. A., *Methods Enzymol.* 31:172–180 (1974).

Struck, et al., *Biochemistry* 20:4083–4099 (1981).

Westhead, E. W., Ann. N. Y. *Acad. Sci.* 493:92–100 (1987).

Wilschut, J., et al., *Biochemistry* 19:6011–6021 (1980).

Wilschut and Papahadjopoulos, Nature (London) 281:690–692 (1979).

Wilson, D. W., et al., *Nature*, 339:355 (1989).

White, J. M., et al., *Ann Rev Physiol*, 52:675 (1990).

BACKGROUND OF THE INVENTION

One of the limiting factors in the pharmacokinetic behavior of many therapeutic drugs is drug uptake by target cells. For many small, uncharged drug compounds, drug permeation across the cell membrane may allow relatively efficient drug uptake by the cell. However, for a variety of larger and/or charged compounds, such as proteins, nucleic acids, and highly water soluble charged organic compounds, passive uptake cell by permeation across the cell membrane may be so limited as to effectively block drug uptake into the cells.

Several methods for enhancing drug uptake into cells have been proposed. In one general approach, a drug is administered in modified or prodrug form, e.g., with masked charged, for transport into cells. The drug can then be enzymatically converted to an active form within the cells.

Alternatively, the drug compound may be coupled to a carrier molecule, such as transfectin, for transport across the cell membrane. Once inside the cell, the carrier moiety may be removed enzymatically, e.g., by an intracellular esterase or protease.

Another approach to enhancing drug uptake by cells exploits the ability of many cells to engulf particles by endocytosis. Here the drug compound is entrapped in particles, typically particles with sizes less than 200–300 $\mu$m, with the particles being administered for targeting to the cells of interest. Liposomes and polymer microparticles are examples of carrier particles that have been used for this purpose.

This approach is limited to certain cell types only, e.g., macrophages, which are active in particle uptake. Another limitation of the approach is that the normal course of intracellular processing involves particle uptake into lysosomes, where the therapeutic compound, e.g., a nucleic acid, can be enzymatically degraded.

Still another approach to enhancing drug uptake by cells involves the use of fusogenic particles designed to fuse with a target cell membrane, releasing the particle contents into the cell interior. Inactivated virus particles have been widely proposed for this purpose, particularly in the context of gene therapy, for introducing large nucleic acid strands into cells. Virus-like particles composed of fusion-promoting viral proteins embedded in artificial lipid bilayer membranes are another example. In both cases, safety concerns and the expense associated with growing, isolating, and deactivating viral components may limit this approach.

It would therefore be desirable to provide a drug-delivery vehicle that substantially overcomes problems associated with present methods of drug delivery to cells, as outlined above.

SUMMARY OF THE INVENTION

In one aspect, the invention includes a vesicle composition for use in delivering a therapeutic agent to target biological cells. The composition includes artificial lipid vesicles (i) composed of vesicles-forming lipids that include at least 10 mole percent of a plasmalogen glyceryl lipid having a small-volume polar head group, e.g., phosphatidic acid, phosphatidyl ethanolamine, and phosphatidyl serine, and (ii) that contain the therapeutic agent in entrapped form. An isolated fusion protein in the composition is effective to facilitate fusion of the lipid vesicles with the cells when the cells, vesicles, and protein are brought together.

The fusion protein may be present in solute form in a suspension of the lipid vesicles, or may be attached to the vesicle surfaces, e.g, by covalent coupling to hydrophilic polymer chains attached to the vesicles, or via a hydrophobic moiety in the protein which anchors the protein to the vesicle membrane.

Where the composition is used for intravenous administration, the vesicles preferably have sizes in the 30–80 nm range, for extended blood circulation lifetime. The vesicles may further include cell-specific targeting molecules carried on the vesicle surfaces for binding the vesicles specifically to target cells.

One preferred composition of vesicle-forming lipids includes 10–80 mole percent plasmalogen phospholipid, 3–15 percent mole negatively charged phospholipid, 10–60 mole percent cholesterol, and 0–40 mole percent neutral phospholipid; preferably 20–40 mole percent plasmenyl ethanolamine, 3–10 mole percent phosphatidylserine, 30–50 mole percent cholesterol, and 20–40 mole percent phosphatidylcholine.

One exemplary fusion protein is an isoform of glyceraldehyde-3-phosphate dehydrogenase. The protein, and its use in promoting membrane fusion, also form part of the invention. Viral fusion proteins represent another class of suitable fusion proteins. Another fusogenic protein useful in the invention is an N-ethylmaleimide (NEM)-sensitive fusogenic protein.

A variety of therapeutic compounds, including nucleic acid strands and nucleic acid analogs, e.g., useful as antisense agents, may be delivered. In one embodiment, the therapeutic agent is a membrane protein or glycoprotein effective to enhance a selected activity of target cells, when incorporated into target-cell membranes, where the therapeutic agent is present in the vesicle membranes which are to be fused with the target cells.

The composition is useful in a method of delivering a therapeutic agent to target cells, by bringing the cells, lipid vesicles, and fusion protein together under conditions suitable for vesicle fusion with the cells.

In a more general aspect, the invention includes a drug-delivery vesicle composition comprising artificial lipid vesicles (i) composed of vesicles-forming lipids that include at least 10 mole percent, and preferably 20–50 mole percent, plasmalogen glyceryl lipid with a relatively small-volume polar head group, and (ii) containing the therapeutic agent in entrapped form.

In one embodiment, the vesicle-forming lipids include 30–70 mole percent plasmenyl ethanolamine and 30–70 mole percent phosphatidylcholine. In another embodiment, the vesicles are composed of between 20–40 mole percent plasmenyl phospholipid with a small volume polar head group, 3–10 mole percent phosphatidylserine, 30–50 mole percent cholesterol, and 20–40 mole percent phosphatidylcholine.

The latter embodiment may further include an isolated fusion protein effective to facilitate fusion of the lipid vesicles with target cells, when the cells, vesicles and protein are brought together.

In still another aspect, the invention provides components for forming a lipid vesicle composition containing first and second reagents capable of interacting with one another. The components include first and second populations of artificial lipid vesicles containing the first and second reagents, respectively. The first population of vesicles is composed of vesicle-forming lipids containing at least 10 mole percent of a plasmalogen phospholipid, and the second population of vesicles is composed of vesicle-forming lipids effective to allow fusion with the first-population vesicles, when the two populations are brought into contact with one another.

The components may further include a fusion protein effective to promote fusion between vesicles in the two different populations.

Plasmenyl phospholipids useful in the invention may be prepared, in accordance with another aspect of the invention, by subjecting at least one ethanolamine glycerophospholipid to an alkaline methanolysis reaction to produce a methanolysis reaction product. The methanolysis reaction product is separated into fractions and a fraction or fractions comprising at least one lysoplasmenyl phospholipids, e.g., plasmenyl ethanolamine, and the head group of the lysoplasmenyl phospholipids, e.g., ethanolamine, is protected with a chemical protection compound. The protected lysoplasmenyl ethanolamine is modified with acyl chloride to give a modified product including at least one protected plasmalogen based phospholipid. Finally, the protected plasmalogen based phospholipid is reacted with a neutral deprotecting agent to give at least one plasmalogen based phospholipid.

These and other objects and features of the invention will be more fully appreciated when the following detailed description of the invention is read in conjunction with the accompanying drawings.

Fluorescence profiles represent the fusion of SUVs comprised of POPS/POPC/16:0–18:1 plasmenyl ethanolamine (1:1:1) (A), POPS/POPC/plasmalogen-depleted bovine brain PE (1:1:1) (B), POPS/POPC/plasmalogen-depleted bovine brain PE (1:1:1) (C), and POPS/POPC/16:0–18:1 phosphatidylethanolamine (1:1:1) (D). Fluorescence tracings were obtained from three independent preparations, performed in quadruplicate, which were averaged after normalization.

Figure 6:
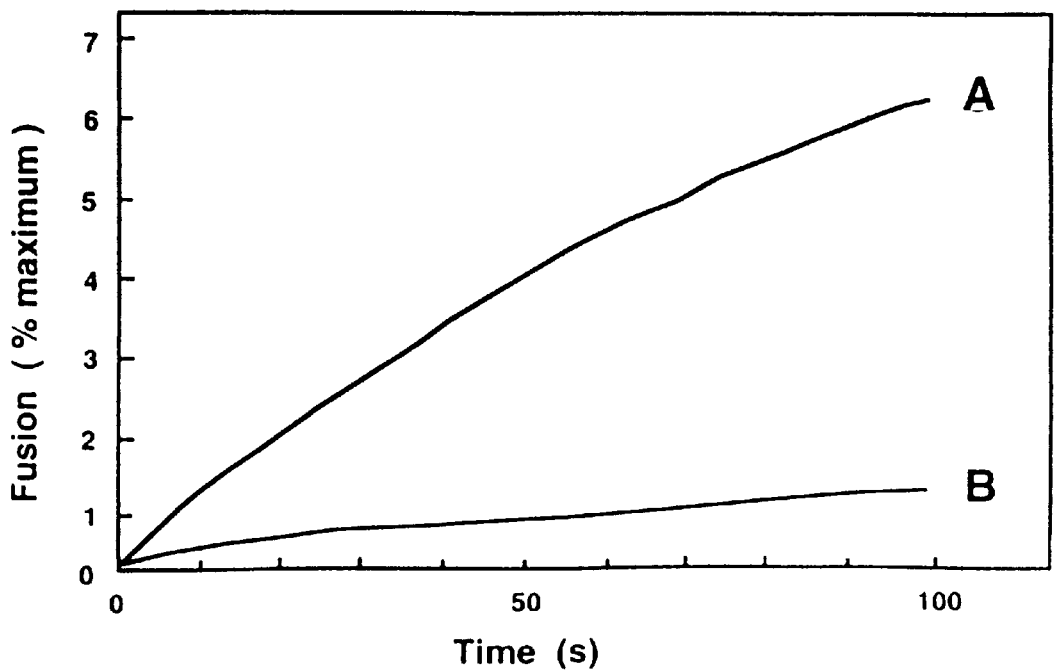

FIG. 6 is a plot of calcium-induced fusion of small unilamellar vesicles comprised of physiologically relevant ratios of phospholipids. Fluorescence profiles represent the fusion of SUVs comprised of POPC/16:0–18:1 plasmenyl ethanolamine/POPS (45:45:10) (A), and POPC/16:0–18:1 phosphatidylethanolamine/POPS (45:45:10) (B). Fluorescence tracings were obtained from two independent preparations, performed in quadruplicate, which were averaged after normalization.

Figure 7:
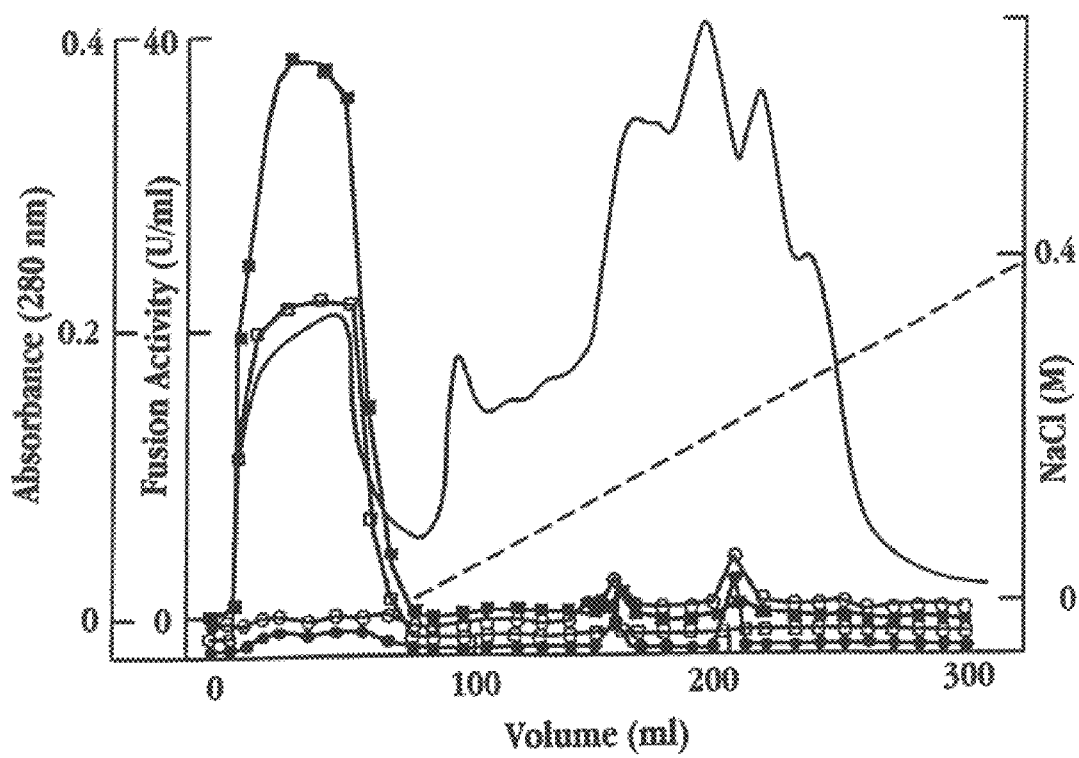

FIG. 7 shows anion exchange chromatography of dialyzed rabbit brain cytosol and characterization of the substrate selectivity of the protein catalyzing membrane fusion. Rabbit brain cytosol was prepared and loaded onto a previously equilibrated DE-52 column. The column was developed with a linear NaCl gradient (0–400 Mm NaCl) and column eluents were assayed for their ability to catalyze membrane fusion utilizing physiologically-modeled small unilamellar vesicles (SUVs) as described in "Materials and Methods". Vesicles were comprised of 16:0–18:1 phosphatidylcholine (27%), 16:0–18:1 phosphatidylserine (6%), cholesterol (40%) and 27% of each of the following ethanolamine glycerophospholipids: 18:0–20:4 plasmenylethanolamine -■-; 16:0–18:1 plasmenylethanolamine -□-; 18:0–20:4 phosphatidylethanolamine -●-; or 16:0–18:1 phosphatidylethanolamine -○-. (——), uv absorbance at 280 nm; (———), NaCl gradient.

FIG. 8a shows Mono Q chromatography of eluents from GTP affinity chromatography containing membrane fusion-catalyzing activity. Active fractions from the GTP-agarose column were pooled, diluted tenfold with equilibration buffer, and loaded onto a Mono Q column. The column was developed with a sodium chloride gradient (———) and aliquots of column eluents were assayed for fusion-catalyzing activity utilizing physiologically-modeled vesicles. The UV absorbing peaks eluting between 13 and 15 ml result from the elution of metabolites, NADH and other non-protein moieties. (——) uv absorbance at 280 nm. FIG. 8b shows an autoradiograph of $^{125}$I Boulton-Hunter labeled and SDS-PAGE separated proteins from both the Mono Q column load and column eluents containing membrane fusion-catalyzing activity.

Figure 9A:
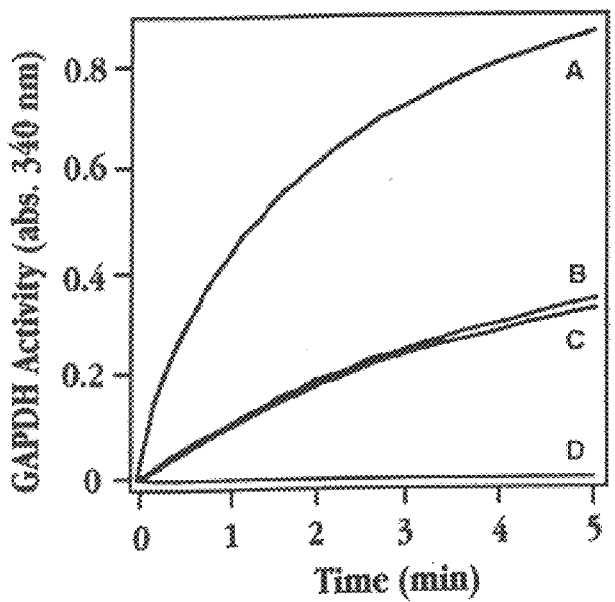
Figure 9B:
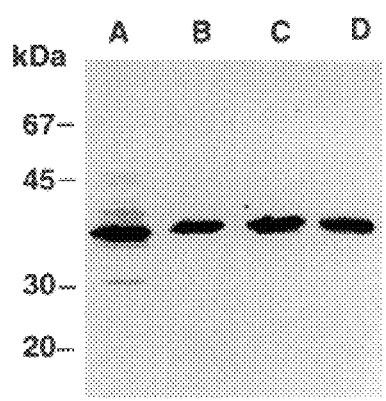

FIG. 9A shows comparisons of glyceraldehyde 3-phosphate dehydrogenase activity and membrane fusion activity in fractions from GTP-agarose and Mono Q chromatographies. Left panel: GAPDH activity was assessed spectrophotometrically by production of NADH. Enzyme aliquots were obtained from either the GTP-agarose affinity column (3 mM GTP eluent (A) or the 20 mM tripolyphosphate/10 mM NAD$^+$ eluent (B)) or from the concentrated void volume of the Mono Q column (C) (concentrated using an Amicon Microcon-10) or from the Mono Q eluents catalyzing membrane fusion activity (D) (also concentrated using an Amicon Microcon-10). FIG. 9B shows SDS-PAGE (10–15% acrylamide PhastGel) analysis of aliquots of enzyme fractions utilized in samples A–D visualized by silver staining.

FIGS. 10A–10C show ethanolamine glycerophospholipid selectivity of the GAPDH isoform mediating membranes fusion at consecutive steps in its purification, including the DE-52 void volume (0.03 mg/ml) (10A), the active fraction eluting from HiLoad SP Sepharose (10B), and the active fraction from GTP-agarose chromatography (10C).

Figure 11:
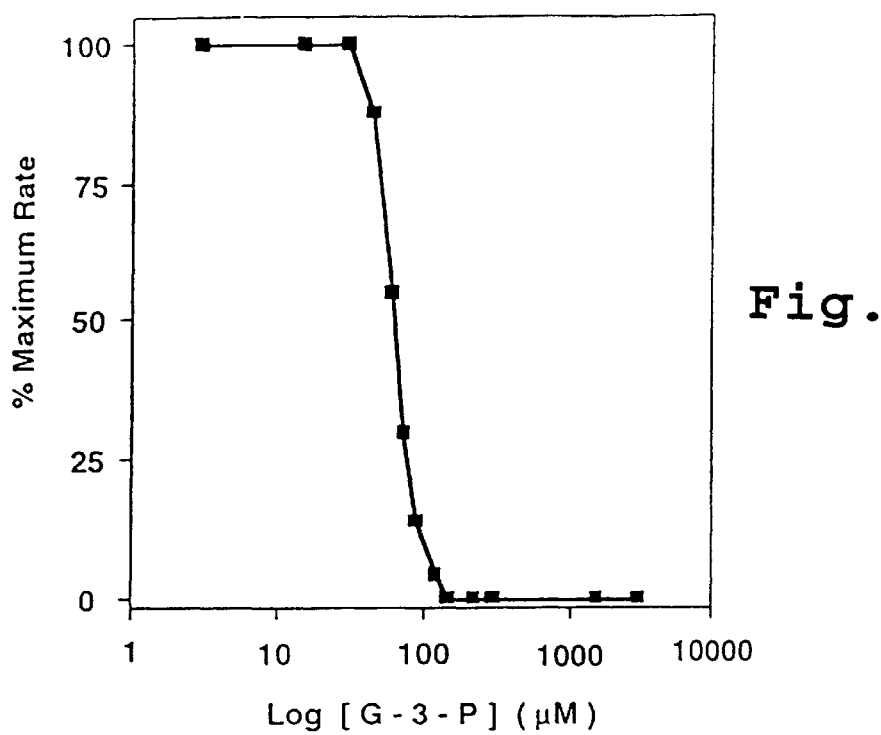

FIG. 11 shows inhibition of GAPDH isoform-catalyzed membrane fusion by (D)-glyceraldehyde 3-phosphate. Physiologically-modeled SUVs were prepared (concentration=200 μM). The other chamber contained the Pi$_3$/NAD$^+$ eluent from GTP-agarose chromatography (0.004 mg/ml) which was previously incubated with (D)-glyceraldehyde 3-phosphate at the indicated concentrations for 30 seconds at 37° C. The rates of membrane fusion from four separate determinations of two preparations were averaged and expressed as a percentage of maximum fusion.

Figure 12A:
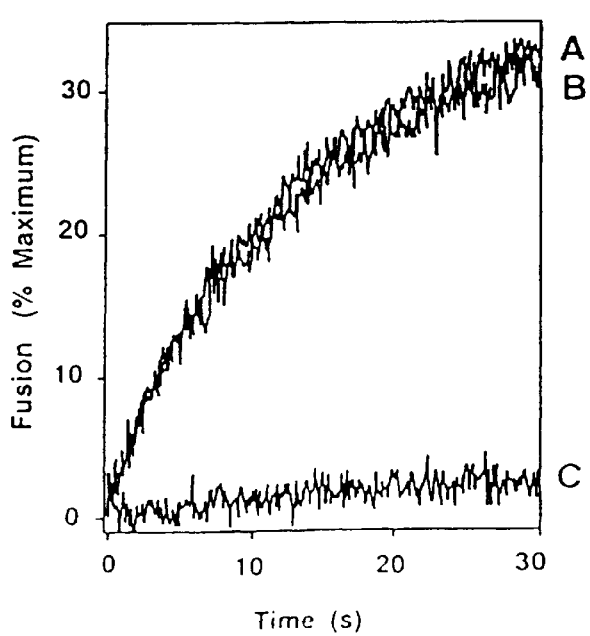
Figure 12B:
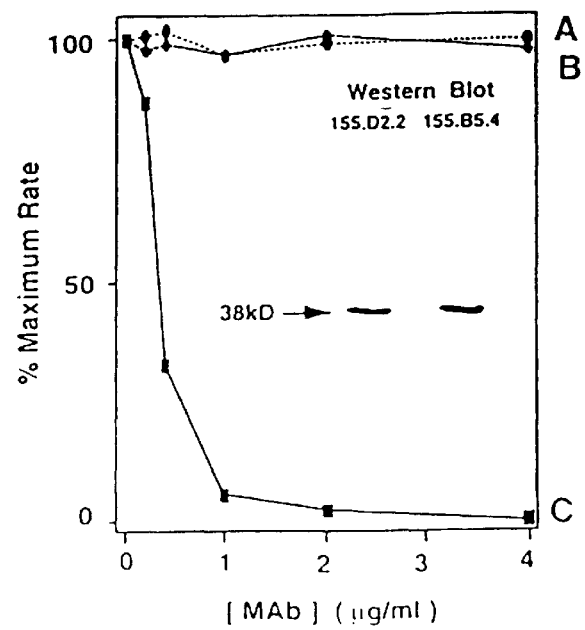

FIG. 12a shows the concentration dependence of the inhibition of membrane fusion activity by the 155.D2.2 monoclonal antibody, and concentration independence of the inhibition of membrane fusion by anti-actin (A) and anti-GAPDH 155.B5.4 (B) monoclonal antibodies. FIG. 12b shows a demonstration of the specificity of both 155.D2.2 and 155.B5.4 for GAPDH when used to probe a Western blot of rabbit brain cytosol separated on 11% SDS-PAGE. The specificity of monoclonal antibodies was determined by visualizing the distribution of bound primary monoclonal antibody after treatment with [$^{125}$-I] rabbit anti-mouse IgG (secondary antibody) and subsequent autoradiography.

Figure 13A:
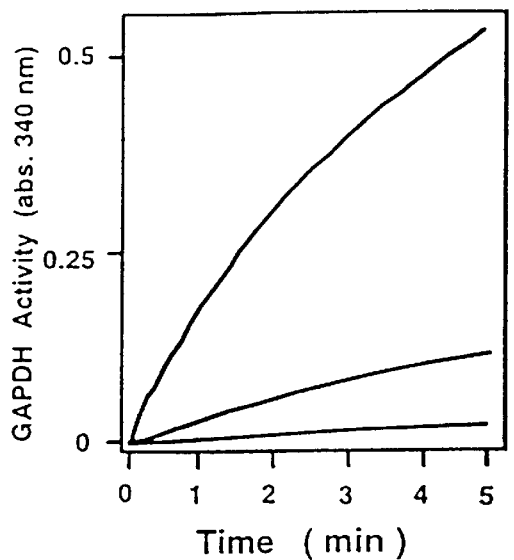
Figure 13B:
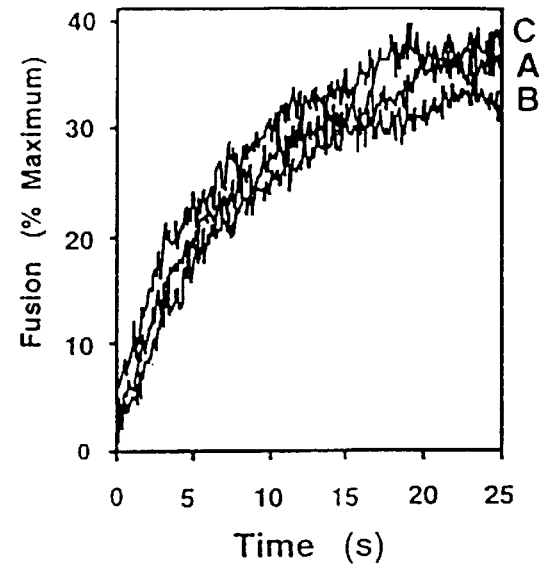

FIGS. 13A and 13B show the inhibition of glyceraldehyde (3)-phosphate dehydrogenase activity (13A), but not membrane fusion activity (13B), by koningic acid.

Figure 14:
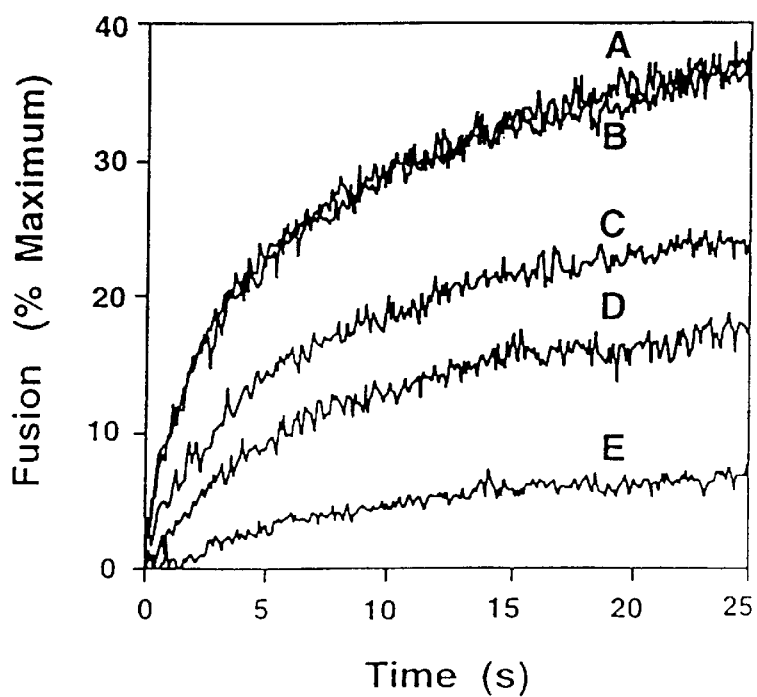
Figure 15:
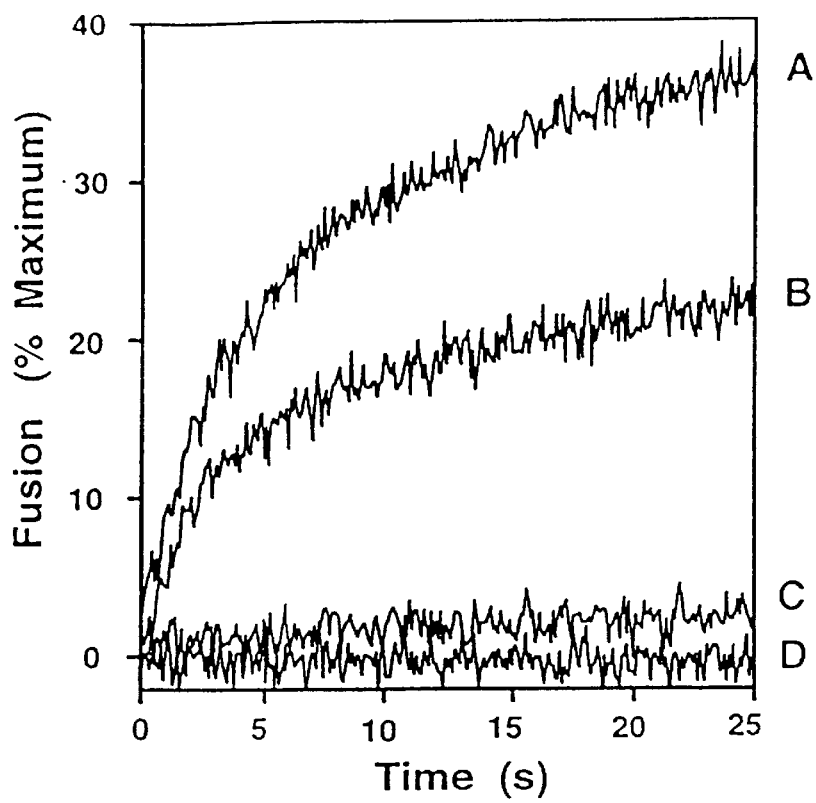

FIG. 14 shows the selectivity of the GAPDH isoform catalyzing membrane fusion for physiologically-modeled vesicles containing distinct mole fractions of plasmenylethanolamine and phosphatidylethanolamine. Physiologically-modeled small unilamellar vesicles consisting of 16:0–18:1 phosphatidylcholine (27%), ethanolamine glycerophospholipid (27%), 16:0–18:1 phosphatidylserine (6%) and cholesterol (40%) were prepared (final lipid concentration of 200 μM) and placed in one chamber of a stopped-flow apparatus. Aliquots of the HiLoad SP Sepharose column eluent (protein concentration=0.002 mg/ml) were placed in the other chamber, samples were rapidly mixed in a stopped flow apparatus and membrane fusion was quantified. Ethanolamine glycerophospholipids included 100% plasmenyl ethanolamine (A) 75% plasmenyl ethanolamine and 25% PE (B); 50% plasmenyl ethanolamine and 50% PE (C); and 25% plasmenyl ethanolamine and 75% PE (D;

FIG. 15 shows the selectivity of the GAPDH isoform catalyzing membrane fusion for physiologically-modeled vesicles containing increasing amounts of PS. Vesicles were composed of 16:0–18:1 PC/18:0–20:4 plasmenyl ethanolamine/cholesterol (27/27/40 mole percent) and varying mole percentages of phosphatidylserine (6% phosphatidylserine (A), 12% phosphatidylserine (B), 3% phosphatidylserine (C) or 0% phosphatidylserine (D)).

Figure 16:
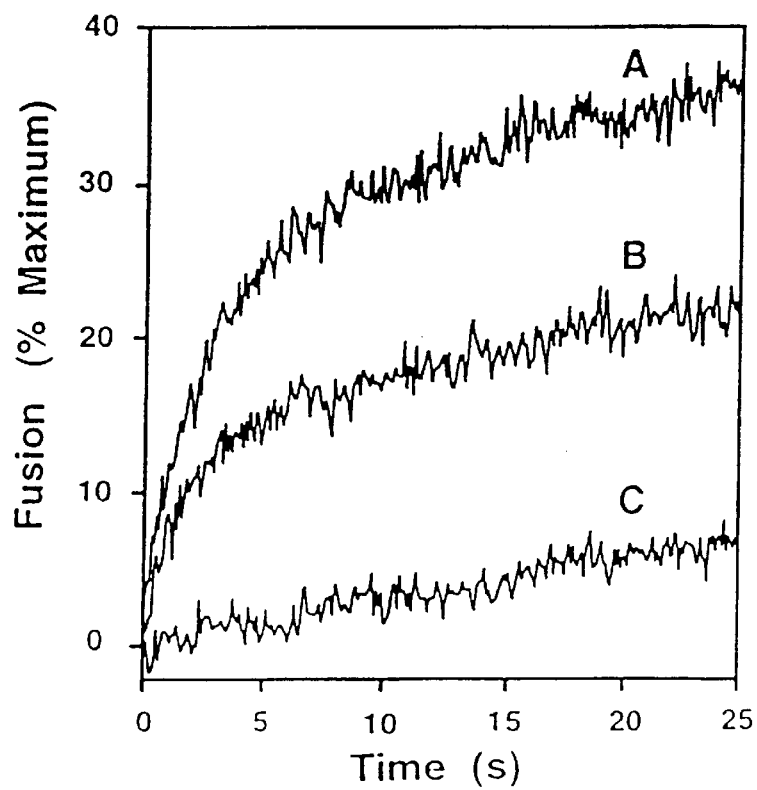

FIG. 16 shows the dependence of GAPDH isoform-catalyzed membrane fusion on the cholesterol content of vesicles. Physiologically-modeled SUVs containing phosphatidylcholine/18:0–20:4 plasmenylethanolamine/phosphatidylserine (45/45/10 mole ratio) and selected mole percentages of cholesterol (i.e., 40% cholesterol (A), 20% cholesterol (B), or 0% cholesterol (C)) were placed in one chamber of a stopped-flow apparatus. The other chamber contained aliquots of the active fraction from GTP-agarose chromatography (i.e., 20 mM tripolyphosphate/10 mM $NAD^+$ ($Pi_3/NAD^+$)), at a protein concentration of 0.004 mg/ml. Samples were rapidly mixed and membrane fusion was quantified. Results represent the average of six recordings from two independent preparations expressed as a percentage of maximal fusion.

DETAILED DESCRIPTION OF THE INVENTION

I. Definitions

Unless otherwise indicated, the terms below have the following definitions herein:

"Artificial lipid vesicles" refers to lipid bilayer vesicle or lipid vesicles prepared from isolated vesicle-forming lipids, typically having a known composition of lipid components.

"Plasmalogen phospholipid" plasmenyl phospholipid, plasmalogen glyceryl, plasmenyl glyceryl and plasmenyl glycerol refer to a vesicle-forming lipid of the form:

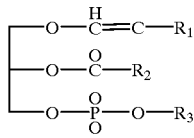

where; $R_1$ and $R_2$ are hydrocarbon chains having lengths from about 8–24 atoms, and which may include unsaturated carbon—carbon bonds, and $R_3$ is a phosphate-attached polar head group, e.g., serine, ethanolamine, choline, or inositol, or a proton (phosphatidic acid) head group.

"Plasmenyl phospholipid with a small-volume polar head group" refers to a plasmenyl phospholipid in which $R_3$ is serine, ethanolamine, small-volume analogs thereof, e.g., cycloserine, monomethylethanolamine or other head groups whose volume is substantially less than that of choline.

"Plasmenyl ethanolamine" or "plasmenyl ethanolamine phospholipid" or "plasmenyl ethanolamine glycerophospholipid" refers to a plasmalogen phospholipid of the type shown above, where $R_3$ is ethanolamine.

"Plasmenyl glyceryl lipid with a small-volume polar head group" includes, in addition to plasmenyl phospholipids with a small-volume polar head group, diacyl glycerol or analog thereof in which one of the hydrocarbon chains in the molecule is linked to the glycerol backbone through a vinyl ether linkage (alkenyl acylglycerol or analog with a small-volume, non-phosphate containing head group).

II. Plasmenyl Phospholipids and Vesicle Fusion

According to one aspect of the invention, it has been discovered that the ability of artificial lipid vesicles to fuse with target cell membranes can be enhanced significantly by addition to the vesicles of plasmenyl glycerol lipid with a small-volume polar head group. This section describes methods of preparing plasmenyl phospholipids of this type, and the fusion properties of lipid vesicles containing such lipids.

A. Preparation of Plasmenyl Phospholipids

Example 1 describes a method for producing a synthetic plasmenyl phospholipid for use in the invention. The method includes the steps of first preparing a plasmenyl phospholipid-containing lipid mixture from a natural source, e.g., brain tissue. The lipid mixture is subjected to alkaline methanolysis to produce a methanolysis reaction products, which are separated into fractions. Fraction(s) containing at least one lysoplasmenyl phospholipid, e.g., plasmenyl ethanolamine, are recovered and the head group, e.g., ethanolamine, of the lysoplasmenyl lipid is protected with a chemical protection compound to give a protected lysoplasmenyl lipid. The protected lysoplasmenyl lipid is modified with acyl chloride to give a modified product including at least one protected plasmalogen based phospholipid. Finally, the protected plasmalogen based phospholipid is reacted with a neutral deprotecting agent to give at least one plasmalogen based phospholipid. This method is described in Glaser, 1994. Other methods of isolating and/or synthetically preparing plasmenyl phospholipids are known.

B. Membrane Fusion Assays

Fusion assays employed to demonstrate vesicle fusion are detailed in Example 2. Briefly, lipid vesicles whose fusion properties are to be tested are mixed with small unilamellar vesicles (SUVs) formed entirely of phosphatidyl serine (PS), which present a highly fusogenic "target". The vesicles to be tested typically are formed by sonication down to SUV sizes, e.g., in the 30–80 nm size range.

Several methods are available for measuring membrane fusion. In the octadecyl ($R_{18}$) fusion assay described in Example 2A, PS SUVs prepared with 4% octadecyl-rhodamine ($R_{18}$) are mixed with unlabeled test vesicles, and membrane fusion is followed by the temporal dequenching of $R_{18}$ observed at 590 nm after excitation at 560 nm.

In the NBD-PE/Rh-PE assay detailed in Example 2B, NBD-PE (N-(7-nitrobenz-2-oxa-1,3-diazol-4-yl)-1,2-dihexadecanoyl-sn-glycerol-3-phosphoethanolamine), and Rh-PE are incorporated into PS SUV's and the vesicles are mixed with test vesicles. Vesicle fusion is followed by the change in fluorescence emission at 530 nm, after emission at 464 nm.

Vesicle contents mixing assays are performed by incorporating DPA (dipicolinic acid) probe into PS SUVs and $Tb(Cl)_3$ into test vesicles. Vesicle fusion is monitored through the formation of the fluorescent Tb/DPA complex measured at >470 nm after excitation at 276 nm.

C. Vesicle Fusion

Figure 1:
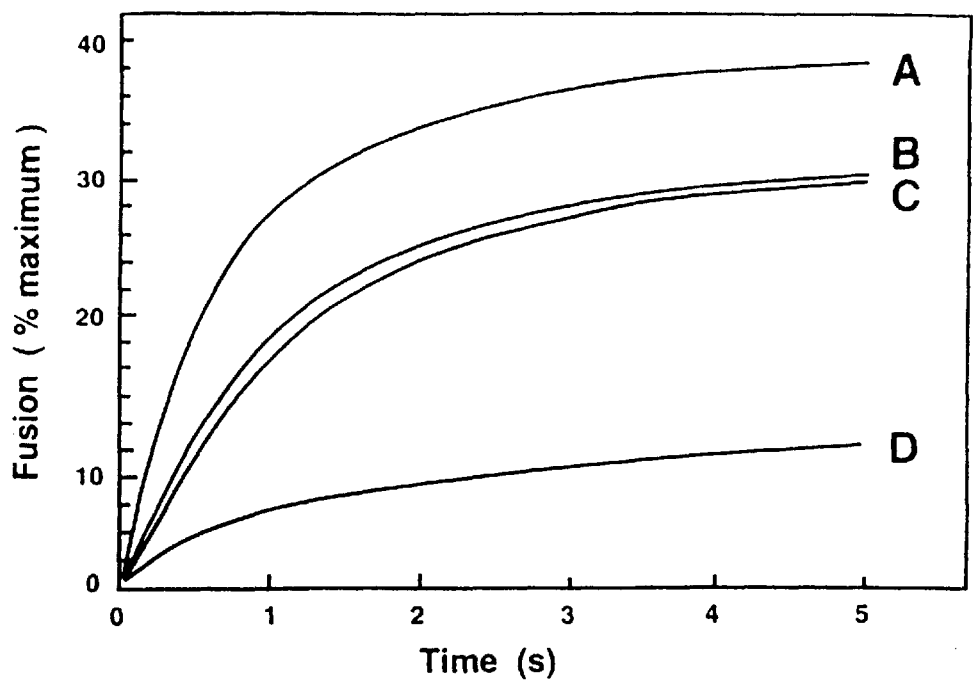
FIG. 1 is a plot of calcium induced fusion of phosphatidylserine lipid vesicles with lipid vesicles comprised of equimolar mixtures of phosphatidylcholine, (PC), and ethanolamine glycerophospholipids. The fluorescence profiles represent the fusion of 16:0–18:1 phosphatidylserine (PS) SUVs with vesicles containing equimolar mixtures of POPC/18:0–20:4 plasmenyl ethanolamine (A), POPC/16:0–18:1 plasmenyl ethanolamine (B), POPC/18:0–20:4 phosphatidyl ethanolamine, (PE), (C), and POPC/16:0–18:1 phosphatidyl ethanolamine (D). Fluorescence tracings from four independent preparations, all performed in triplicate, were averaged after normalization to the maximum fluorescence increase which would occur after all vesicles fused.

The effect of plasmenyl phospholipids and phospholipid acyl chain lengths on rates of vesicle fusion, in SUVs composed of equimolar amounts of PC and plasmenyl PE or PE was investigated. As seen in FIG. 1, plasmenyl ethanolamine lipids vesicles (plots A and B) gave substantially higher rates of fusion than corresponding vesicle formulations containing the PE (plots C and D, respectively), and longer acyl chain lengths (18:0, 20:4) in both plasmenyl and PE phospholipids (plots A and C) gave substantially higher fusion rates than phospholipids with shorter acyl chain lengths (16:0, 18:1).

It should be noted that vesicles containing plasmenyl ethanolamine did not induce alterations in the calcium profile or threshold of vesicle fusion. Both semisynthetic 18:0, 20:4 plasmenyl ethanolamine and 18:0, 20:4 plasmenyl ethanolamine purified from canine myocardium gave identical fusion results. Additionally, measured fusion rates of PC/PE vesicles containing the $R_{18}$ label to labeled PS SUVs were identical to those obtained in systems containing the $R_{18}$ label in the PS SUVs.

Figure 2:
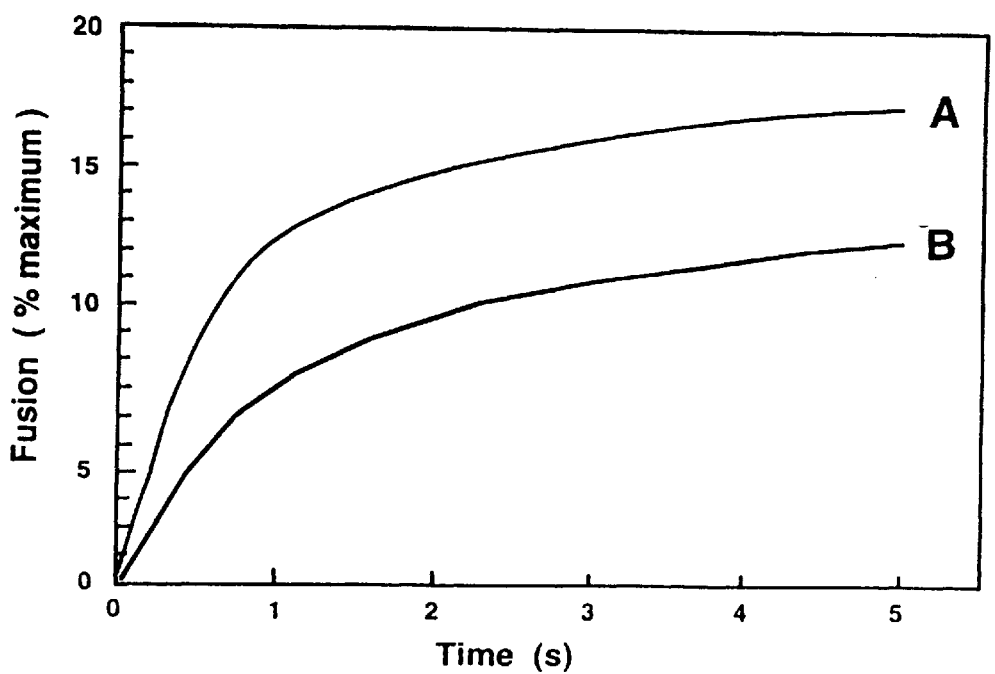
FIG. 2 is a plot of the comparison of the effect of endogenous or plasmalogen-depleted bovine brain ethanolamine glycerophospholipids on calcium-induced fusion of phosphatidylserine lipid vesicles with phosphatidylcholine/ethanolamine glycerophospholipid (1:1) lipid vesicles. Fluorescence profiles represent the fusion of 16:0–18:1 phosphatidylserine SUVs with vesicles containing equimolar mixtures of POPC/bovine brain PE (A), or POPC/plasmalogen-depleted bovine brain PE (B). Fluorescence tracings from four independent preparations, all performed in triplicate, were averaged after normalization.

FIG. 2 shows a comparison of control and plasmalogen-depleted bovine brain ethanolamine glycerophospholipids in a PC/PE and PS vesicle fusion system. The results demonstrate that vesicles containing native bovine brain ethanolamine glycerophospholipids (plot A) were twice as fusogenic as those containing plasmalogen-depleted ethanolamine glycerophospholipids (plot B). Bovine brain PE, which contains a mixture of both plasmalogen and diacyl-PE, supports a fusion rate that falls between that of mixed vesicles containing only plasmalogen PE and those containing only diacyl-PE as shown by comparing FIGS. 1 and 2. Plasmalogen-depleted bovine brain PE supported vesicle fusion rate similar to those manifested by phosphatidylethanolamine containing oleic acid at the sn-2 position.

Similar results were obtained in the NBD-PE fusion assay. Vesicles composed of equal molar mixtures of PC and 16:0–18:1 plasmenyl ethanolamine fused to PS SUVs three times more rapidly fused than vesicles comprised of equal molar mixtures of PC and 16:0–18:1 phosphatidylethanolamine, as determined by the dequenching of NBD-PE fluorescence by Rh-PE as a surface area increased after vesicle fusion. Although detailed full time course kinetic analysis of vesicle fusion processes demonstrates substantial complexity, the results herein largely reflect differences in the initial rates of membrane fusion where contribution from second order processes are minimized.

Figure 4:
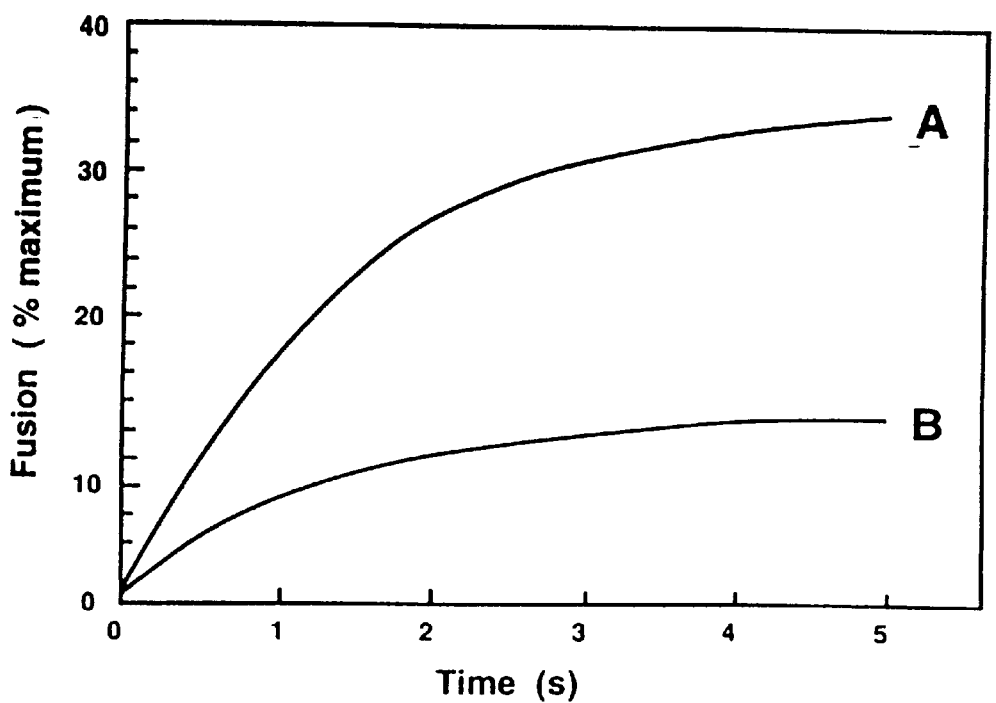
FIG. 4 is a plot of terbium/dipicolinic acid (Tb/DPA) assay of calcium induced fusion of phosphatidylserine lipid vesicles with lipid vesicles comprised of equimolar mixtures of phosphatidylcholine and ethanolamine glycerophospholipids. Fluorescence profiles represent the fusion between 16:0–18:1 phosphatidylserine SUVs and vesicles containing equimolar mixtures of POPC/16:0–18:1 plasmenyl ethanolamine (A) or POPC/16:0–18:1-phosphatidylethanolamine (B). Fluorescence tracings from three independent preparations, all performed in quadruplicate, were averaged after normalization to the maximum fluorescence increase which would occur after all vesicles fused.

Similar results were also obtained in a contents mixing assay, as seen in FIG. 4. The fusion of vesicles composed of PS with vesicles of equimolar mixtures of PC/PE for both 16:0–18:1 plasmenyl ethanolamine and 16:0–18:1 phosphatidyl ethanolamine exhibit a time course, initial rate, and extent similar to that observed in the $R_{18}$ fusion assay (compare FIG. 4 to FIG. 1). The positive correlation of rate constants derived from contents mixing and lipid mixing fusion assay shows that the lipid-mixing assays reflect, in large part, bona fide membrane fusion and do not reflect vesicle apposition and lipid transfer.

It is known that lipid vesicles having a smaller diameter and higher radius of curvature, and consequently more internal strain, exhibit faster fusion rates in general than those having a larger diameter, a lower radius of curvature and less internal strain. To verify that observed differences in fusion rates were attributable to properties of the vinyl ether linkage and did not result from differences in vesicle size, the diameter of diacyl-plasmalogen-containing vesicles using [$^{14}$C] inulin was compared. There were no significant differences in size between the various binary mixtures of PC and PE SUVs comprised of distinct ethanolamine glycerophospholipid subclasses as seen in Table I. The diameter of PS vesicles were approximately 1.2 times larger than SUVs comprised of equal molar mixtures of choline and ethanolamine glycerophospholipids.

TABLE I

| Vesicle Incorporation of [$^{14}$C] inulin | |
|---|---|
| Incorporated/μmole Liposome Composition | [$^{14}$C] inulin of Lipid (DPN) |
| Phosphatidylserine | 72,500 ± 4,600 |
| POPC/16:0–18:1 | 43,600 ± 3,700 |
| Plasmenylethanolamine POPC/16:0–18:1 | 43,200 ± 3,200 |
| Phosphatidylethanolamine POPC/Bovine Brain PE | 40,900 ± 3,000 |

Figure 5:
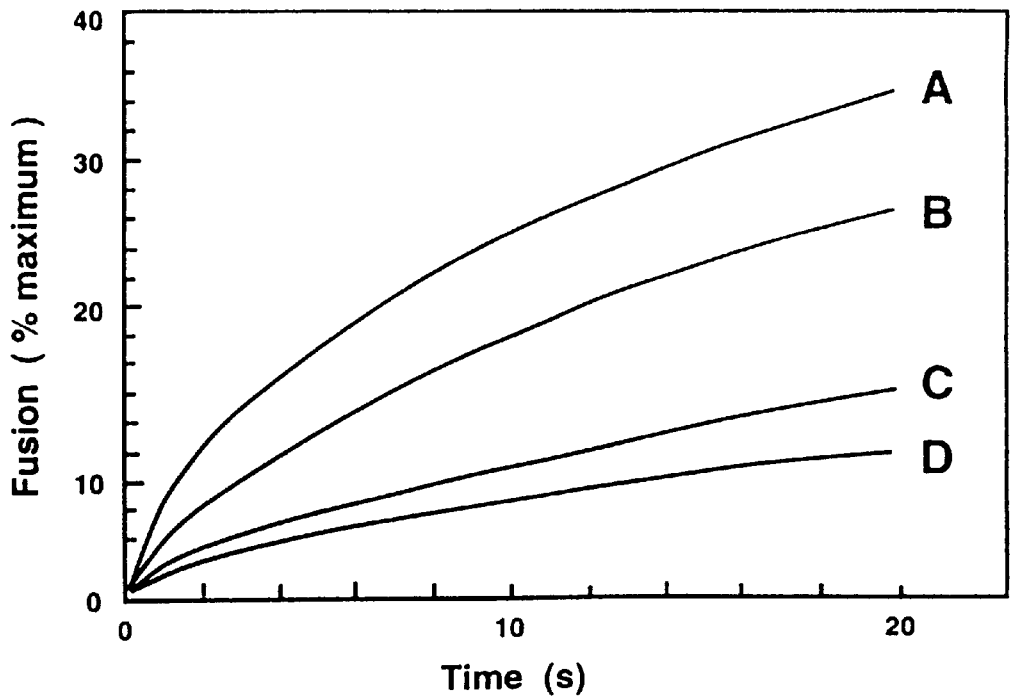
FIG. 5 is a plot of calcium-induced fusion of vesicles comprised of equimolar ternary mixtures of serine, choline, and ethanolamine glycerophospholipids.

The effect of plasmenyl ethanolamine lipids on lipid vesicle fusion in vesicles containing more complex lipid mixtures of PS, PC, and plasmenyl lipids was also examined with the $R_{18}$ fusion assay. The assay results are found in FIG. 5.

The presence of plasmenyl ethanolamines induces an even greater increase in relative membrane fusion rates in this liposome fusion system. Vesicles containing 16:1–18:1 plasmenyl ethanolamine were six times more fusogenic than those containing 16:0–18:1 phosphatidylethanolamine. Similarly, vesicles containing bovine brain PE were more than twice as fusogenic as those containing plasmalogen-depleted PE in this system. To approach even more closely the physiologic complement of phospholipid classes in a synaptic vesicle, lipid vesicles comprised of 45% PC/45% PE/10% PS were also assayed and the results are found in FIG. 6. Although fusion rates were significantly slower in this system in comparison to the previous systems, vesicles containing 45% 16:0–18:1 plasmenyl ethanolamine demonstrate an initial rate of membrane fusion significantly greater than vesicles containing corresponding amounts of 16:0–18:1 phosphatidylethanolamine.

The results of these experiments demonstrate that the covalent nature of the sn-1 aliphatic constituents in glycerophospholipids is an important determinant of the rate of membrane fusion. More generally, enhanced vesicle fusion is observed in lipid vesicles containing at least 10 mole percent, and preferably 30–70 mole percent of a plasmenyl phospholipid containing a small-volume head group. These results are substantiated through fast-flow kinetic analysis using multiple independent methods to quantify membrane fusion, including both lipid-mixing and internal contents mixing fusion assays.

D. Plasmenyl-Vesicle Composition

In one aspect, the invention includes a lipid vesicle composition which exploits the greater fusogenic activity of lipid vesicles containing plasmalogen glyceryl lipids with small-volume polar head groups. In particular, the vesicles containing such lipid, in an amount of at least 10 mole percent, are used for delivery of a therapeutic agent entrapped in the vesicles for delivery to a target cell.

The entrapped therapeutic agent may be any of a large number of agents that can be entrapped in lipid vesicles, including water-soluble agents that can be stably encapsulated in the aqueous compartment of the vesicles, lipophilic compounds that stably partition in the lipid phase of the vesicles cells, or agents that can be stably attached, e.g., by electrostatic attachment to the outer vesicle surfaces. Exemplary water-soluble compounds include small, water-soluble organic compounds, peptides, proteins, oligonucleotides and gene fragments.

Lipid vesicles containing the plasmalogen lipids and an entrapped agent are prepared according to well-known methods, such as hydration or a lipid film, reverse-phase evaporation, and solvent infusion. Other lipid vesicles components used in the preparation of the vesicles include conventional phospholipids, such as PC, PS, and/or PE, and may also include cholesterol or cholesterol analogs. One preferred composition, disclosed in Example 3, includes equimolar amounts of PC and plasmenyl PE.

Another preferred lipid composition, particularly for use in a lipid composition in combination with a fusion protein (Section 3 below) includes 20–40 mole percent plasmenyl phospholipid, 3–10 mole percent phosphatidylserine, 30–50 mole percent cholesterol, and 20–40 mole percent PC.

Where the composition is used for intravenous administration, the vesicles are preferably SUVs, i.e., in the size range 30–80 nm, for longer circulation time. Methods for producing sized liposomes, e.g., by sonication or extrusion through defined pore-size membranes are well known.

The vesicles may be further designed, e.g., by the addition of surface receptors or ligands, for cell-specific binding to target cells.

The vesicles are employed, in one general application, for delivery of a therapeutic agent to target cells, via vesicle fusion with the target cell plasma membrane. A biologically active agent can also be disposed within a bilayer of a vesicle and transferred to a cell using the compounds of this invention whereby the compound or compounds, disposed within the lipid bilayer, becomes integrated within the cell membrane.

In another general application, the vesicle composition is used as an anti-viral agent, acting as a target-cell decoy for virus circulating in the bloodstream. This application relies on the ability of a virus fusion protein to catalyze the fusion to plasmalogen containing bilayer membranes, discussed in the section below.

III. Protein-Mediated Vesicle Fusion

In accordance with another aspect of the invention, it has been discovered that plasmalogen-containing lipid vesicles are rapidly fused with bilayer membranes in the presence of fusion proteins, including a newly discovered fusion protein that has been identified as an isoform of glyceraldehyde-3-phosphate dehydrogenase (GAPDH).

A. Isolation and Characterization of GAPDH Isoform

The isolation of a GAPDH isoform that has been discovered to catalyze vesicle fusion, in accordance with the invention, is described in Example 5. Briefly, a mouse-brain homogenate was centrifuged at high speed to produce a cytosol. Dialyzed cytosol was fractionated on a DE-52 column, and the fractions were assayed in a vesicle fusion assay. The lipid vesicles that were used in the assay were composed of 27 mole percent of a selected PC lipid, one composition with plasmalogen ethanolamine, 6 mole percent PS, 40 mole percent cholesterol, and 27 mole percent PC. These vesicles show little measurable self-fusion activity, as evidenced by change in fluorescence in an $R_{18}$ assay (half of the vesicles labeled with $R_{18}$). The cytosol itself showed no measurable ability to catalyze the fusion of the vesicles, either for plasmalogen or PE containing vesicles. However, the void volume from the column showed high vesicle fusion activity. Surprisingly, this activity was confined to vesicles containing plasmalogen phospholipids (FIG. 7). The reasons underlying the cryptic nature of this activity in crude cytosol have been elaborated, showing that the cytosol contains a potent endogenous protein inhibitor of fusion activity.

Fractions from the void volume containing fusion-catalyzing activity were pooled, filtered and loaded onto a HiLoad SP Sepharose column. After extensive washing, proteins with membrane fusion activity were eluted utilizing a nonlinear sodium chloride gradient from 0 to 0.5 M NaCl. Active fractions were pooled, and loaded onto a GTP-agarose column. After extensive washing, fractions were eluted with 5 mM GMP, 3 mM GTP, and finally in buffer alone. Membrane fusion activity was eluted with 20 mM tetrasodium tripolyphosphate and 10 mM $NAD^+$.

GTP-agarose affinity eluents were further purified either by reverse phase HPLC (in preparation for protein sequencing) or by Mono Q anion exchange chromatography. Active fractions were pooled, and loaded onto a Mono Q PC 1.6/5 column previously equilibrate buffer C at a flow rate of 200 μl/minute. Fusion-catalyzing activity was eluted using a continuous gradient from 0 to 500 mM NaCl. The fraction associated with fusion activity is shown in FIG. 8. At this stage, a final preparation was obtained which was 790-fold purified. A substantially pure protein band was obtained on SDS PAGE (sodium dodecyl sulfate polyacrylamide gel electrophoresis). The purified protein migrated with a molecular weight of 38 kDal.

The membrane fusion protein, purified as described above, was applied to a Vydac Reverse Phase HPLC column. A single homogeneous 38 kDa band was obtained and submitted for N-terminal Edman degradation sequencing. Twenty-three amino acids of N-terminal sequence were obtained and found to be homologous to GAPDH.

TABLE II

Sequence of the Membrane Fusion Protein and Homology with GAPDH

| | |
|---|---|
| VKVGVNGFGRIGRLVTRAAFNSG | Membrane Fusion Protein |
| VKVGVNGFGRIGRLVTRAAFNSG | Human GAPDH (muscle) |
| VKVGVNGFGRIGRLVTRAAFNSG | Human GAPDH (liver) |
| VKVGVNGFGRIGRLVTRAAFNSG | Bovine GAPDH |
| 1    5    10    15    20    aa | |

The following evidence demonstrated that the isolated fusion protein is an isoform of GAPDH:

1. Western blots of the purification fractions from above, including the final purification material, all showed a single 38 kDal when probed with anti-GAPDH antibody (prepared as in Example 5).

2. The N-terminal sequence of the isoform is identical with that of several GAPDH enzymes from several sources (Table II above).

3. Membrane fusion activity was inhibited by D-glyceraldehyde 3-phosphate with a $K_i$ similar to the association constant of glyceraldehyde 3-phosphate with GAPDH (FIG. 11).

4. A monoclonal antibody directed against GAPDH (i.e., antibody 155.D2.2) specifically inhibited membrane fusion in a dose-dependent manner, while other monoclonal antibodies (e.g., either other antibodies directed against GAPDH (e.g., 1.55.B5.4) or those directed against other non-relevant proteins (e.g., actin)) did not inhibit membrane fusion activity even at concentrations of monoclonal antibody which were 10-fold higher than those which inhibited fusion activity (FIG. 12).

5. Koningic acid, a known inhibitor of GAPDH enzyme activity (Sakai, et al., 1991) which covalently binds to the active site cysteine (cysteine 149) failed to inhibit membrane fusion activity at concentrations which maximally inhibited GAPDH enzyme activity (FIGS. 13A and 13B).

Further characterization of the membrane fusion-catalyzing activity in the void volume demonstrated that it was trypsin-sensitive, calcium-independent, neutral-active (maximal activity was present between pH 6 and 7), heatlabile (activity was ablated by heating for 3 minutes at 90° C.), and inactivated by DTNB (1 mM for 30 minutes at 37° C.) but was not inhibited by N-ethylmaleimide (1 mM for 60 minutes at 37° C.) (data not shown). Furthermore, membrane fusion activity catalyzed by void volume eluents was not due to the fusion of labeled $R_{18}$ vesicles with endogenous lipid carried through in the void volume since dequenching of $R_{18}$ fluorescence did not occur in the absence of added acceptor vesicles.

Examination of the tissue specificity of the fusion activity revealed appreciable levels only in brain and muscle (rabbit hind leg muscle) with only diminutive amounts of activity present in liver and kidney (100-fold less than that manifest in brain). Finally, a crude surgical separation of rabbit brain white matter from gray matter demonstrated that fusion activity in void volume eluents derived from gray matter was threefold higher than those derived from white matter (data not shown). Thus, the void volume from anion exchange chromatography of rabbit brain cytosol contains a tissue-specific protein that catalyzes the calcium-independent fusion of membrane bilayers containing plasmenylethanolamine but not phosphatidylethanolamine.

B. Lipid Vesicle Composition and Fusion Properties

Studies were carried out in support of the invention to determine optimal lipid composition for protein-catalyzed vesicle fusion. First, the ethanolamine glycerophospholipid subclass requirements of the fusion protein at each stage of the purification procedure were examined. Membrane fusion activity was highly selective for vesicles containing plasmenylethanolamine (compared with phosphatidylethanolamine) at each stage of the purification procedure (FIGS. 10A–10C). Furthermore, a 2- to 4-fold selectivity for plasmalogens containing arachidonic acid in comparison to oleic acid at the sn-2 position (synaptic membranes are substantially enriched in arachidonic acid-containing molecular species) was observed.

To quantify the dependence of membrane fusion activity on the fractional percent of plasmenylethanolamine present in the vesicles undergoing membrane fusion, the mole fraction of ethanolamine glycerophospholipids represented by plasmenyl ethanolamine was varied from 0–100%. Membrane fusion activity increased as the mole fraction of plasmenylethanolamine in the vesicles was increased up to 75% plasmenylethanolamine with no additional increment at higher plasmenylethanolamine mole fractions (FIG. 14).

To determine the importance of serine glycerophospholipids and cholesterol in facilitating fusion mediated by the purified protein, fusion rates were quantified in vesicles containing selected concentrations of phosphatidylserine (0–12 mole %) and cholesterol (0–40 mole %). In vesicles in which the serine glycerophospholipid content was varied from 0–12%, the most rapid rates of membrane fusion were present in vesicles containing 6 mole % PS (FIG. 15) (note that this approximates the percentage of PS found in synaptosomal membranes (Westhead, 1987; Cullis and Hope, 1991). Importantly, vesicles containing only 3% PS or less could not be induced to fuse by the membrane fusion protein under the conditions employed. Vesicles containing 12 mole % PS fused at rates that were considerably less than those manifest at 6 mole % PS, demonstrating that neither bulk alterations in membrane surface charge nor alterations in physical properties of the vesicle is the sole mechanism through which changes in PS content facilitate protein-mediated membrane fusion (in contrast to non-protein-mediated $Ca^{2+}$-dependent vesicle fusion)

Next, the concentration of cholesterol in the vesicles was varied from 0–40 mole %. The membrane fusion protein possessed an obligatory requirement for cholesterol, with little or no fusion manifest in vesicles lacking cholesterol (FIG. 16). Protein-facilitated membrane fusion activity induced by cholesterol increased in a dose dependent fashion with the most rapid rates of membrane fusion manifest in vesicles containing a physiologic complement of cholesterol (i.e., 40 mole %). Collectively, these results demonstrate that the membrane fusion activity has an obligatory requirement for physiologic complements of plasmenyl phospholipid with small-volume polar head group—in this case, ethanolamine—a negatively charged phospholipid, e.g., PS, and cholesterol, and will not rapidly catalyze membrane fusion in the absence of any one of these constituent lipids of synaptic vesicles and the plasma membrane.

The kinetics of GAPDH isoform-catalyzed membrane fusion was calculated from the high-resolution stopped-flow fusion measurements made above. Calculations of fusion rates were based on the protein concentration of 4 $\mu$g/ml and vesicle concentration (800 $\mu$m lipid, utilizing the assumptions that ≈1000 molecules of lipid are in each vesicle and that the active form of GAPDH is a tetramer (similar to the active form of the dehydrogenase). Utilizing these assumptions, the GAPDH isoform catalyzed the fusion of one pair of vesicles in 1 ms (on average). Since many rounds of vesicle fusion are catalyzed during each assay, it is evident that the fusion protein represents a true catalyst of vesicle fusion and does not mediate the fusion of vesicles in a stoichiometric fashion (i.e., hundreds of vesicle pairs undergo fusion mediated by one GAPDH tetramer during each assay).

IV. Fusion-Vesicle Composition and Method

This section describes a vesicle composition for use in delivering a therapeutic agent to target biological cells, in accordance with the invention. The composition includes artificial lipid vesicle composed of vesicles-forming lipids that include at least 10 mole percent of a plasmalogen glyceryl lipid with a small-volume polar head group, and an isolated fusion protein effective to facilitate fusion of the lipid vesicles with the cells, when the cells, vesicles and protein are brought together. The therapeutic agent is entrapped in the vesicles.

A. Lipid Vesicles

The lipid vesicles in the composition are formed as above by standard vesicle-forming methods. The lipids employed in the vesicles include at least 10 mole percent of a plasmenyl phospholipid with a small-volume polar head group, e.g., ethanolamine, serine, or phosphatidic acid. Alternatively, the plasmenyl lipid may be diacyl glycerol analog, where one of the hydrocarbon chains is linked to the glycerol backbone through a vinyl ether linkage. The amount of the plasmenyl glycerol lipid is preferably between about between 20–70 mole percent, more preferably 20–40 mole percent.

In accordance with the studies discussed above, the lipid mixture also include 3–15 mole percent of a negatively charged phospholipid, e.g., PS or PA, preferably about 3–10 mole percent PS. One exemplary formulation includes 20–40 mole percent plasmenyl phospholipid, 3–10 mole percent phosphatidylserine, 30–50 mole percent cholesterol, and 20–40 mole percent PC. It will be appreciated that the negatively charged phospholipid may 28 be contributed by the plasmenyl phospholipid itself, e.g., by plasmenyl Ps.

The vesicles also contain cholesterol or a cholesterol analog, e.g., ergosterol, in an amount preferably between 20–50 mole percent cholesterol, more preferably between 30–40 mole percent. The balance of the lipids, if any, is preferably made of PC, in an amount between 0–40 mole percent, preferably 20–40 mole percent. Other vesicle-forming lipids, or lipids that are stably anchored in a lipid bilayer, such as alpha-tocopherol, may be included.

Lipid vesicles containing the plasmalogen lipids and an entrapped agent are prepared according to well-known methods, as described above. Typically, vesicles are formed by hydration of a lipid film, where the compound to be delivered is either included in the lipid film, in the case of a lipophilic compound, or is included in the hydration medium, in the case of a water-soluble therapeutic agent. Alternatively, the therapeutic agent may be loaded into preformed vesicles, e.g., by loading an ionizable compound against a pH gradient.

Where the composition is used for intravenous administration, the vesicles are preferably SUVs, i.e., in the size range 30–80 nm, for longer circulation time. Methods for producing sized liposomes, e.g., by sonication or extrusion through defined pore-size membranes are well known. The vesicles may be further designed, e.g., by the addition of surface receptors or ligands, for cell-specific binding to target cells.

B. Fusion Protein

The fusion protein in the composition is a protein effective to catalyze the fusion of artificial lipid vesicles to target biological cells, i.e., mammalian cell membranes. More particularly, the fusion proteins in the invention are characterized by the ability to catalyze rapid fusion of lipid vesicles having the lipid composition described above, e.g., 20–40 mole percent plasmenyl ethanolamine, 3–10 more percent PS, 20–40 mole percent cholesterol and 20–40 percent PC. As demonstrated in the studies above, protein-catalyzed fusion occurs to a substantial extent within a few seconds of mixing vesicles and protein, whereas no measurable fusion is observed in the absence of the protein.

One preferred protein in the composition is the GAPDH isoform described in Section III. Additionally, a fusion protein which has been described in relation to vesicle-mediated transport in both mammalian and yeast cells is the so-called NEM (N-ethylmaleimide)-sensitive fusion protein (NSF) and related fusion protein SEC18 (Wilson). Further, peptide fragments of these proteins which retain fusion active are also considered herein to be fusion proteins.

A large number of viral fusion proteins that catalyze viral fusion reactions either under acidic or pH independent conditions have also been described (White, Blobel, Edwardson, Epand, Fredericksen, Ito, Morrison, and Rapaport). Many of these proteins have hemagglutinin activity (White, Tsurodome). All viral proteins studies to date are class I integral proteins having external N 25 termini and internal C termini with a membrane spanning anchoring region. A large number of viral proteins have been cloned and can be prepared by standard recombinant techniques (White).

Because the fusion protein is capable of promoting the fusion of vesicles in suspension, it must either be maintained separate from the vesicles, prior to use, or maintained in the presence of an inhibitor of the protein's vesicle-fusion activity. Thus, for example, when the vesicles are administered intravenously for vesicle fusion at a target site, the fusion protein may be administered as a separate agent, e.g., in solution or carried on non-fusogenic lipid vesicles, to provide therapeutic vesicles and fusion protein at the in vivo target site.

Alternatively, the fusion protein may be present in a suspension of the therapeutic vesicles in a composition that also contains a soluble inhibitor of protein-catalyzed vesicles fusion. For example, where the fusion protein is GAPDH isoform, high concentrations of glutaraldehyde-3-phosphate or high concentration of a low-affinity anti-GAPDH antibody may be employed (see FIGS. 11 and 12B). One inhibitor of GAPDH isoform fusion which has been discovered herein is a 55 KDal tubulin protein isolated from brain cytosol, prepared according to the isolation procedures detailed in Example 6. In studies performed in support of the invention, it was found that:

1. tubulin-Sepharose affinity columns specifically bind GAPDH isoform;
2. tubulin-mediated inhibition of GAPDH isoform catalyzed membrane fusion was not attenuated by large increases in vesicle concentration;
3. tubulin-mediated inhibition of membrane fusion was stoichiometric with GAPDH; and
4. tubulin-mediated inhibition of GAPDH-catalyzed membrane fusion was dependent upon the residence time of tubulin with GAPDH isoform, and independent of contact time of tubulin with vesicles.

In the case of NEM-sensitive fusion protein, the inhibitor of membrane fusion may be a suitable reducing agent, e.g., N-ethylmaleimide. Alternatively, the inhibitor can be a low-affinity antibody present in amount effective to block vesicle fusion in the composition. Similarly in the case of viral fusion proteins, low-affinity antibodies or specific fusion-blocking factors are present when the protein and vesicles are combined in the vesicle composition.

In this general embodiment in which fusion protein and vesicles are present in a single suspension prior to use, the fusion protein may be present as a soluble factor in the aqueous suspension medium of the vesicles, or may be attached to the surfaces of the vesicles, or a subpopulation thereof. In the latter case, the protein may be covalently attached directly to the vesicle surfaces, or attached covalently to a hydrophilic polymer chain, such as a polyethyleneglycol chain, which is itself coupled to a lipid vesicle lipid. Methods for direct covalent attachment of proteins to liposomes are well known, as are lipid conjugates containing a hydrophilic polymer.

In some case, particularly viral fusion proteins, the protein itself may have a hydrophobic transmembrane region which allows the protein to be anchored in he lipid vesicles.

C. Applications

The vesicle-fusion protein composition is designed for use in delivering an agent or compound to a target cell, either at an in vivo site or to cultures of cells in vitro. The delivery is accomplished by fusion of the vesicles with the plasma membrane of the target cells, in the presence of the fusion protein. Several applications are discussed below.

1. Introducing Genetic Material into Cells In Vitro

Recombinant DNA techniques routinely involve introduction of heterologous genes into animal or plant cells in culture. In this general application, the genetic material to be transferred is encapsulated within fusogenic vesicles constructed according to the method. The vesicles are added to the recipient cells in the presence of a fusion protein, with vesicle fusion to the cells leading to direct introduction of the encapsulated material into the cells.

2. Gene Therapy

For gene therapy uses, fusogenic vesicles containing encapsulated therapeutic genes are administered, e.g., intravenously, for targeting to cells lacking the replacement gene carried in the vesicles. The vesicles may be surface modified for targeting to the cells of interest, as described above. The fusion protein may be administered separately, for migration to the target site independent of the vesicles, or may be co-administered as a single suspension with the vesicles, or may be attached to the vesicles. In the latter case, vesicle fusion is prevented during vesicle storage by the presence of a soluble inhibitor. After administration, dilution and clearance of the inhibitor in the bloodstream allows vesicle fusion with target cells to occur at the target site.

C. Addition of Membrane Factors to Target Cells

A unique therapeutic application provided by the invention is the ability to introduce cell membrane factors, e.g., ion channel proteins, ligand-specific glycoproteins, and various receptor proteins into the membrane of target cells. In this application, the therapeutic vesicles are prepared with the cell membrane factor incorporated into the vesicle bilayer membranes. Vesicles of this type may be constructed either by diffusing membrane proteins into lipid vesicles, e.g., in the presence of a surfactant, or by forming adding the membrane factor to either the lipid film or aqueous hydration medium used in forming the vesicles.

Administration of the vesicles and fusion protein is as described above; that is, the fusion protein is administered either separately, or together with the vesicles in a suspension also containing a fusion-protein inhibitor. The membrane factors in the vesicle membranes are incorporated into target cell membrane with vesicle fusion to the target cells.

4. Direct Compound Delivery to Target Cells

As noted above, a variety of therapeutic compounds, including generally charged compounds, peptides, and nucleic acids, may have limited therapeutic applications because of the problem of low uptake into target cells. Using the vesicle composition of the present invention, entrapped therapeutic compounds can be delivered to target cells with high uptake via vesicle-cell fusion. Administration of the vesicles and fusion protein is as described above.

V. Mixed Vesicle Composition

The mixed-vesicle composition of the invention includes two separate populations of fusogenic vesicles, each containing a reagent or reagents capable of interacting with the reagent or reagents present in the other population. The purpose of the two-component vesicle composition is to form fused vesicles that contain both reagents, where for a variety of reasons, it is advantageous to combine the two reagents under selected conditions. The composition may contain vesicles capable of fusing under non-catalyzed conditions, i.e., in the absence of a vesicle fusion protein, or may contain the two populations of vesicles in combination with a vesicle-fusion protein.

A. Non-Catalyzed Components

In this embodiment, the two populations of vesicles have compositions which allow fusion in the absence of a vesicle-fusion protein. Two exemplary lipid compositions are the ones employed in the vesicle-fusion assays described in Section II. As will be recalled, one population of the vesicles in these assays contained equimolar ratios of plasmenyl PE and PC, and the second, PS alone. More generally, the first population contains at least 10 mole percent, preferably 30–70 mole percent, of a plasmenyl glycerol lipid with a small-volume polar head group, such as plasmenyl ethanolamine. The second population contains a highly fusogenic lipid composition, such as one containing 50–100 mole percent PS or other glycerol lipid, such as diacyl glycerol, capable of forming an inverted hexagonal phase ($H_{II}$).

Other lipid compositions may be suitable. For example, in the assays described in Section II, vesicles formed with equimolar amounts of PE and PC, particularly PE having acyl chains of 18 carbon atoms or more, were found to be fusogenic with PS vesicles.

Each vesicle component is formed as above with an encapsulated reagent or reagent entrapped in the vesicle bilayer phase. The vesicles may be sized and otherwise processed, e.g., to remove non-entrapped material, as detailed above.

Representative applications of the two-vesicle system are discussed in Section V-C below. In general, the two vesicle populations are mixed under conditions which lead to rapid vesicle fusion, e.g., 1–5 seconds, although some applications will not require rapid vesicle fusion, and thus may employ lipid compositions and/or fusion conditions that lead to vesicle fusion only after a period of several minutes or longer.

B. Catalyzed Fusion Components

In this second embodiment, the two populations of vesicles have compositions which allow rapid fusion only in the presence of a vesicle-fusion protein. The lipid compositions described in Section III are exemplary, particularly for use with the GAPDH isoform protein. More generally, for use with this protein, the vesicles may each be composed of between 20–40 mole percent plasmenyl glycerol lipid with a small-volume polar head group, 3–10 mole percent phosphatidylserine, 30–50 mole percent cholesterol, and 20–40 mole percent phosphatidylcholine.

The two populations of vesicles are formed as above with an encapsulated reagent or reagent entrapped in the vesicle bilayer phase. The vesicles may be sized and otherwise processed, e.g., to remove non-entrapped material, as detailed above.

In the applications discussed in Section V-C below, the catalyzed-fusion system has the advantages that (i) vesicle fusion and thus reagent mixing occurs at catalytic rates, e.g., within a msec, and (ii) both vesicle populations may have the same lipid composition.

C. Applications

1. Kinetic Studies. It is typically necessary, when conducting kinetic studies of enzymes or other biological systems, to mix the interacting components at a well defined time point. For example, ATP utilizing systems can be studied kinetically by photolytic cleavage of ATP releasing molecules, to achieve precisely timed introduction of ATP into the system. Similar kinetic studies require precise introduction of protons to an enzyme mixture, and such studies have been carried out heretofore with photolytically generated proteins.

In the present application, the biological system, e.g., enzyme, and substrate, e.g., ATP or protons, are packaged in the two vesicle populations and brought together under rapid mixing conditions, preferably employing a catalyzed fusion reaction. Reaction events are then followed by suitable reporter means, e.g., change in florescence signal.

Since vesicles in this system will fuse at different rates, it may be necessary to study changes induced by a fusion event involving a single vesicle from each population. Ideally, the vesicles used in single-vesicle studies of these types would employ large unilamellar vesicles, in the size range typically from 2–20 microns, which can be formed by known methods, e.g., reverse evaporation phase vesicle formation. Single fusion events can be monitored in a number of ways, e.g., by fluorescence microscopy. Large vesicle fusion may require fusion protein catalysis for achieving reasonable fusion rates.

2. Microassays. A related application uses the vesicle fusion system for biochemical assays, particularly where the assay can be carried out on a micro scale. By way of example, a body-fluid sample, such as a serum-sample, contained is a fusogenic lipid vesicle is added to vesicle(s) containing assay reagents in a micro-scale assay device under vesicle-fusion conditions. After fusion, the presence or absence of analyte in the sample can be monitored by a color or fluorometric change in the fused vesicle(s), or the presence of electrochemical species, such as $H_2O_2$, produced in the vesicle(s) and measurable by known microelectronic devices.

3. Drug Loading. For many drugs, drug loading efficiency and stability in lipid vesicles is limited by drug diffusion from the vesicles after loading. One approach to this problem is to selectively precipitate the drug once it has been loaded. This may be done, in accordance with the present invention, by fusing drug-loaded vesicles with a second population of vesicles containing a drug-precipitating agent, such as a divalent metal, or other complexation agent, or a buffering agent effective to lower the pH of the fused vesicles.

4. Drug Activation. Some drugs can be loaded and/or stored advantageously in lipid vesicles in an inactive, prodrug form. Just prior to use, the loaded compounds can be converted to an active form by fusing vesicles containing the prodrug with vesicles containing an activating agent, e.g., an esterase or protease enzyme. Alternatively, one or both of the different reagents may include small organic molecules which, when brought together, produce an active-drug complex, or undergo a chemical reaction leading to an active drug.

The following examples illustrate various methods for preparing fusogenic vesicles, a fusion protein, a fusion-protein inhibitor, and methods of demonstrating the fusogenic properties of the vesicle compositions. The examples are intended to illustrate the invention, but in no way limit its scope.

Materials

Bovine brain ethanolamine glycerophospholipids, 1-palmitoyl-2-oleoyl-sn-glycero-3-phosphoserine, I-palmitoyl-2-oleoyl-sn-glycero-3-phosphocholine and 1-palmitoyl-2-oleoyl-sn-glycero-3-phosphoethanolamine were purchased from Avanti Polar Lipids (Birmingham, Ala.). Cholesterol was obtained from Nu Chek Prep (Elysian, Minn.). Octadecylrhodamine (R18), Tb(Cl)3, and dipicolinic acid (DPA) were purchased from Molecular Probes (Eugene, Oreg.). DE-52 anion exchange resin was purchased from Whatman (Maidstone, EN). DTT was purchased from Calbiochem (San Diego, Calif.), and GTP and GMP were purchased from Beckman (Indianapolis, Ind.). Multiphor 2-D electrophoresis supplies including Immobilines II were purchased from Pharmacia Biotech Inc. (Piscataway, N.J.). HPLC-grade solvents were purchased from Baxter Scientific (McGaw Park, Ill.). Most other chemicals were obtained from Sigma (St. Louis, Mo.).

Phospholipids were purified to remove trace contaminants on an Altex Ultrasphere-Si column (4.6 mm×25 cm) utilizing a mobile phase comprised of hexane/isopropanol with a 1–7% $H_2O$ gradient (Geurts van Kessel, et al., 1977).

Plasmenyl ethanolamines (16:0–18:1) plasmenyl ethanolamine and 18:0–20:4 plasmenyl ethanolamine) were synthesized as described previously (Glaser and Gross, 1994; Han, et al., 1992), and as detailed in Example 1A. Octadecylrhodamine was purified on an Altex Ultrasphere CN column (4.6 nm×25 cm) utilizing a mobile phase comprised of acetonitrile and a gradient of triethanolamine (20 mm to 50 mm, pH 7.0 with acetic acid) over 40 ml at a flow rate of 2.0 ml/min. Purified R18 fractions were extracted using a modified Bligh and Dyer and were stored under nitrogen at −20° C. in chloroform.

EXAMPLE 1

Preparation of Plasmenyl Ethanolamine

A. Synthesis of Plasmenyl Ethanolamine

Bovine brain ethanolamine glycerophospholipids (1 g/100 mL chloroform) were subjected to alkaline methanolysis by mixing with 0.5 N methanolic NaOH (100 mL) for forty-five minutes at 25° C. The reaction was stopped by addition of 50 mL of 1 N acetic acid and placed in a separatory funnel. After gentle mixing, the lower phase was collected and dried under vacuum at room temperature. The resultant yellow paste was dissolved in 6 mL of chloroform, filtered, and injected onto a Dynamax Preparatory Si HPLC column (31.4 mm×20 cm) previously equilibrated with chloroform. After 20 minutes of elution with chloroform at a flow rate of 10 mL\min., a linear gradient to 100% methanol over 100 min. was initiated. Lysoplasmenyl ethanolamine eluted at 60% methanol, was detected by TLC (Whatman LKG plates) using another mobile phase (system A, 95:35:6 chloroform\methanol\water, v\v\v) by subsequent iodine staining (lysoplasmenyl ethanolamine $R_f$=0.17).

Lysoplasmenyl ethanolamine-containing fractions were pooled, dried under nitrogen, and resuspended in chloroform at a yield of 80% of theoretical. The ethanol amine head group was then blocked using a N-9-fluorenylmethoxylcarbonyl (Fmoc) protection group. Protection of the primary amine was affected by stirring 170 mg of lysoplasmenyl ethanolamine (0.37 mmol) in distilled $CHCl_3$ (distilled over $P_2O_5$) with a 5-fold molar excess of succinimidylfluroenylmethoxyl-carbodiimide (600 mg, 1.85 mmol) and 240 mg (3.7 mmol) of imidazole for four hours at room temperature. A second addition of 240 mg of succinimidyl-Fmoc (0.74 mmol) and 100 mg of imidazole (1.48 mmol) was performed, and the reaction was stirred overnight at 25° C. prior to the separation of the reaction products by the method of Bligh and Dyer (1959).

Purification of Fmoc-lysoplasmenyl ethanolamine was accomplished using straight phase HPLC employing a chloroform\methanol linear gradient as described above, with Fmoc-LPE eluting at 20% methanol. Fractions containing Fmoc-LPE ($R_f$=0.29 in TLC neutral system A) were pooled, dried under vacuum, resuspended in chloroform for storage, and stored under an atmosphere of nitrogen.

50 mg (0.072 mmol) of Fmoc-lysoplasmenyl ethanolamine was dried under nitrogen and resuspended in chloroform (2 mmol) under anhydrous conditions, and, after addition of recrystallized DMAP (10 mg, 0.082 mmol), the appropriate fatty acid anhydride or acyl chloride was added in 4–10-fold molar excess (100–200 mg) and stirred for 6 hours at 35° C.

Dicyclohexylcarbodiimide (in 1-mg iterative additions) was added to reactions to regenerate the anhydride every two hours. The reaction was quenched by addition of one-quarter volume of methanol (1 mL) and neutral deprotection of the Fmoc group was accomplished by addition of one-quarter volume of diethylamine and subsequent stirring for eight hours at room temperature.

The resultant plasmenyl ethanolamine was purified after Bligh and Dyer extraction with a Dynamax Preparatory Si HPLC column (21.4 mm×25 cm) previously equilibrated with hexane\isopropanol\water\ammonium hydroxide (48:48:4:0.005,v\v) as the mobile phase employing a 4–8.5% $H_2O$ gradient, as described in Blank & Snyder (1983). Fractions containing plasmenyl ethanolamine were pooled and further purified on an Altex Ultrasphere-Si column (4.6 mm×25 cm) with a mobile phase of hexane\isopropanol (50:50, v\v) with a 1–7% $H_2O$ gradient (Geurts van Kessel, et al., 1977). A total of 27 mg of arachidonoylated plasmenyl ethanolamine was obtained. Individual molecular species of plasmenyl ethanolamine (either 16:0, 18:0, or 18:1 at the sn-1 position) were resolved on a Beckman C18 reverse-phase HPLC column (4.6 mm×25 cm) using a mobile phase comprised of methanol\acetonitrile\water (90.5:2.5:7,v\v) containing 20 nM choline chloride as described previously by Gross (1984). The purity of plasmenyl ethanolamine was assessed by TLC employing neutral system A, a base system (65:25:5 chloroform\methanol\ammonium hydroxide), and an acid system (6:8:2:2:1 chloroform\acetone\methanol\acetic acid\water). The concentration of phospholipids was quantified by capillary gas chromatography following derivatization by acid methanolysis as described previously by comparisons with internal standard.

B. Preparation of Plasmalogen-Depleted Bovine Brain Ethanolamine Glycerophospholipids Plasmenyl ethanolamine was selectively removed from total bovine brain ethanolamine glycerophospholipids by exploiting the acid lability of the vinyl ether linkage.

Bovine brain ethanolamine glycerophospholipids (15 mg) were dried under nitrogen and subsequently exposed to HCl fumes for 25 minutes. After two minutes of flushing with nitrogen, the sample was resuspended in chloroform, and plasmalogen-depleted PE was isolated on an Altex Ultrasphere-Si column (4.6 mm×25 cm) using a mobile phase of hexane\isopropanol (50:50 v\v) with a 1–7% $H_2O$ gradient. The fatty acid compositions of bovine brain PE in plasmalogen-depleted bovine brain PE were quantified by capillary gas chromatography after acid methanolysis. The results are found in Table III below.

TABLE III

Fatty Acid and Aldehyde Composition of Ethanolamine Glycerophospholipids

| Depleted Carbon Chain Glycerophospholipids | Bovine Brain Ethanolamine Glycerophospholipids | Plasmalogen -Bovine Brain |
|---|---|---|
| plasmal 16:0 | 6.5 ± 0.8 | 0.5 ± 0.3 |
| acyl 16:0 | 3.5 ± 0.3 | 6.8 ± 0.7 |
| plasmal 18:0 | 11.1 ± 0.5 | 1.3 ± 0.2 |
| acyl 18:0 | 13.0 ± 0.4 | 33.1 ± 2.0 |
| plasmal 18:1 | 15.6 ± 1.0 | 0.5 ± 0.7 |
| acyl 18:1 | 17.6 ± 0.9 | 22.6 ± 0.6 |
| acyl 20:4 | 13.4 ± 0.7 | 12.5 ± 0.6 |
| acyl 22:4 | 6.6 ± 1.3 | 5.7 ± 0.1 |
| acyl 22:5 | 4.1 ± 0.7 | 5.1 ± 1.3 |
| acyl 22:6 | 8.4 ± 0.4 | 10.3 ± 2.0 |

EXAMPLE 2

Vesicle-Fusion Assays

A. Octadecyl ($R_{18}$) Fusion Assay

Phospholipids used for fusion assays were co-dissolved with lipid fluorescent probes in chloroform, evaporated under nitrogen, and evacuated for one hour at 100 mTorr. Multilamellar lipid vesicles were formed by resuspension of liposome buffer A (100 mM $NaCl_2$, 5 mM Na HEPES, 0.1 mM EGTA, pH 7.4) and vigorous vortexing. Small unilamellar vesicles (SUVs) were formed by sonicating the multi-lamellar lipid vesicles for five minutes at 46° C. using a 40% duty cycle at a power level of 1.5 with a Vibra Cell sonicator equipped with a medium tip.

All lipid vesicles were used immediately after preparation and were maintained under a nitrogen atmosphere during all steps in the procedure. The octadecyl ($R_{18}$) fusion assay was performed as in Hoekstra, et al., in 1984, with the following modifications. Phosphatidylserine vesicles were prepared with 4% $R_{18}$ and were mixed with an equal molar amount of labeled vesicles comprised of 50% 16:0–18:1 phosphatidylcholine and 50% ethanolamine glycerophospholipid. This mixture was loaded into one chamber of an SLM-Amino spectroflurometer equipped with an SLM stopped-flow apparatus (model no. FP-052). The other chamber was loaded with liposome buffer alone or with liposome buffer containing an addition, 20 mM $CaCl_2$. The contents of the chambers were rapidly mixed (dead time 7 ms) in a 1:1(v/v) ratio.

Fusion was monitored by the temporal dependence of $R_{18}$ dequenching observed at 590 nm after excitation at 560 nm. The final total lipid concentration in assays was approximately 200 micromolar. The 0% fusion level was assessed by monitoring fluorescence when the vesicles were mixed at 0 mM $CaCl_2$. The 100% fusion level was measured by preparing lipid vesicles comprised of the mixture which would result if all vesicles fused and subsequently quantifying the resultant $R_{18}$ fluorescence. Fluorescence readings were normalized using the 0% and 100% fusion levels and were expressed as a percentage of maximum fusion ($F_{max}$). The reported initial rates (expressed in terms of $F_{max\%}^{2-1}$) represent predominantly fusion rates under the conditions employed since the high $Ca^{2+}$ concentration used in conjunction with the use of SUVs each predispose to membrane fusion, Wilschut, et al. (1980).

B. NBD-PE/Rh-PE Assay

This assay was performed by preparing phosphatidylserine SUVs containing 1.8% Rh-PE and 1.2% NBD-PE and adding an equimolar amount of unlabelled PC/PE vesicles pursuant to (Struck, et al. (1981); and Hoekstra, 1982). Fusion was monitored by NBD-PE fluorescence at 530 nm after excitation at 464 nm. The 100% fusion level was assessed by preparing lipid vesicles composed of 46.5% PS, 25% PC, 25% PE, 0.9% Rh-PE, and 0.6% NBD-PE and subsequently quantifying fluorescence intensity.

Since Rh-PE partially quenches NBD-PE fluorescence by resonance energy transfer at the initial concentrations used in these experiments, membrane fusion results in an increase in NBD-PE fluorescence as available membrane surface area increases.

C. Contents Mixing Assay

Vesicles for use in a contents mixing assay were prepared by first resuspending phospholipids in either 20 mM $NaCl_3$ 50 mM DPA, and 5 mM Na HEPES (pH 7.4) pursuant to Wilschut and Papahadjopoulos (1979); Wilschut, et al. (1980), Düzgünes, et al. (1987).

SUVs containing entrapped $TbCl_3$ or DPA were separated from unencapsulated probe by gel filtration chromatography employing a Sepharose 6B column equilibrated with 100 mM NaCl, 5 mM Na HEPES, and 1.0 mM EDTA, pH 7.4. An aliquot of the vesicle-containing fraction was subjected to Bligh and Dyer extraction, acid methanolysis, and capillary gas chromatography to quantify the liposome lipid concentration for subsequent fluorescence assays. Contents-mixing assays were performed by incorporating the DPA probe into PS SUVs and Tb probe into PC/PE SUVs. After mixing in equal molar concentrations and loading into the stopped-flow apparatus, fusion was monitored through the formation of fluorescence Tb/DPA complex measured at >470 nm after excitation at 216 nm. Final total lipid concentration in the assay were approximately 200 µM. The 100% fusion level was assessed by measuring the fluorescence of vesicles prepared in a buffer of 10 mM NaCl, 25 mM sodium citrate, 1.25 mM $TbCl_3$, 25 mM DPA, and 5 mM Na HEPES (pH 7.4) and processed as described above. All fusion assays were performed at 37° C.

EXAMPLE 3

Plasmenyl Ethanolamine-Mediated Vesicle Fusion

A. Purified Plasmenyl Lipids

Small unilamellar vesicles (SUVs) composed of equal molar ratio of choline and various purified ethanolamine glycerophospholipids, including plasmenyl ethanolamines, were added in equal parts to PS SUVs containing $R_{18}$, prepared as described in Example 2. The rate of liposome fusion was quantified by stop-flow kinetics through measurement of the increased $R_{18}$ fluorescence intensity, which reflects its attenuated quenching as the effective membrane and surface area of the probe distribution increases after fusion with an unlabeled vesicle, with the results shown in FIG. 1, and discussed above.

To verify the differences in observed fusion rates were not due to selective breakdown of one subclass of ethanolamine glycerophospholipid, aliquots of lipid vesicles employed in the fusion studies were extracted by the method of Bligh and Dyer and analyzed by TLC and straight-phase HPLC. No lysophospholipids or other contaminants were detected within the time frame of the assay. For higher sensitivity detection, 16:0–18:1 plasmenyl ethanolamine was synthesized with a $^3$H label on the sn-2 oleoyl group. This label was added to a liposome preparation containing unlabeled PC and PE. No significant generation of radiolabeled fatty acid or lysophospholipid was observed during the procedures employed.

B. Plasmalogen-Depleted Bovine Brain PE

Plasmalogen-depleted bovine brain PE were prepared as described in Example 1B. No significant changes were observed in the percentages of polyunsaturated fatty acids at the sn-2 position in this function.

Small unilamellar vesicles (SUVs) composed of equal molar ratio of phosphatidylcholine and bovine brain PE or POPC/plasmalogen-depleted bovine brain PE were added in equal parts to PS SUVs containing $R_{18}$, as above. The rate of liposome fusion was quantified by stop-flow kinetics through measurement of the increased $R_{18}$ fluorescence intensity, with the results shown in FIG. 2, and discussed above.

C. NBD-PE/Rh-PE Assay

Figure 3:
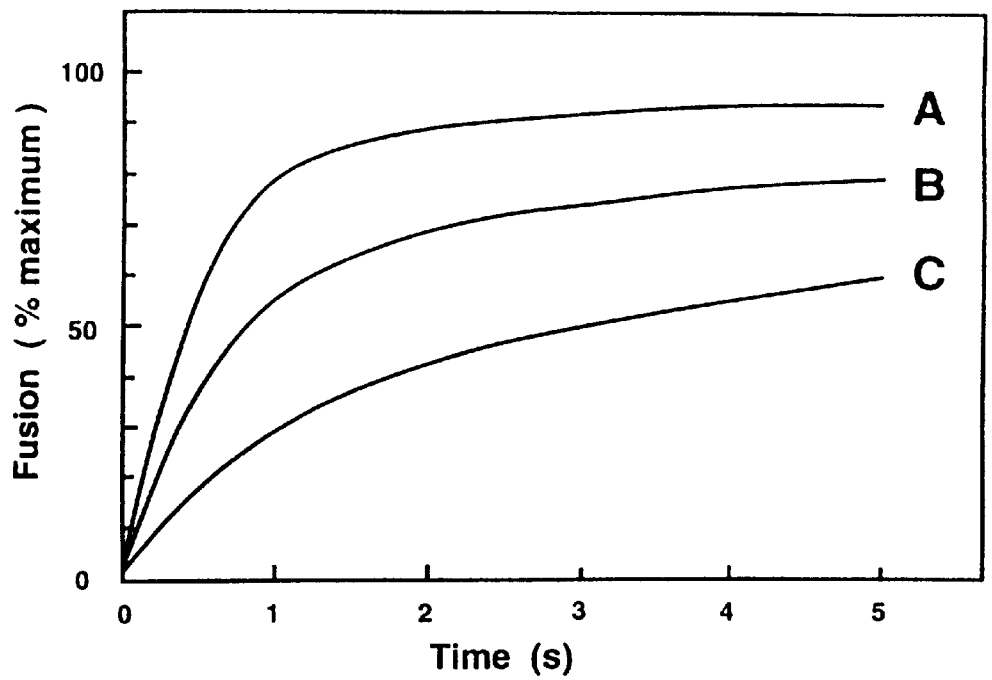
FIG. 3 is a plot of N-(7-nitrobenz-2-oxa-1,3-diazol-4-yl)-1,2-dihexadecanoyl-sn-glycerol-3-phosphoethanolamine/N-(lissamine rhodamine B sulfonyl)-1,2-dihexadecanoyl-snglycero-3-phosphoethanolamine (NBD-PE/Rh-PE) fusion assay of calcium-induced fusion of phosphatidylserine lipid vesicles with lipid vesicles comprised of equimolar mixtures of phosphatidylcholine and ethanolamine glycerophospholipids. Fluorescence profiles represent the fusion of 16:0–18:1 phosphatidylserine SUVs with vesicles containing equimolar mixtures of POPC/16:0–18:1 plasmenyl ethanolamine (A), POPC/bovine brain PE (B), and POPC/16:0–18:1 phosphatidylethanolamine (C). Fluorescence tracings were obtained from two independent preparations, performed in quadruplicate, which were averaged after normalization.

To verify the results obtained with the $R_{18}$ fusion assay, a second lipid-mixing assay utilizing NBD-PE and Rh-PE was used. Phosphatidylserine (PS) SUVs containing 1.8% Rh-PE and 1.2% NBD-PE were mixed with equimolar amounts of unlabelled PC/PE vesicles, where the PE species was either plasmenyl ethanolamine (16:0–18:1), brain PE, or phosphatidylethanolamine (PE). The fusion kinetics were examined as described in Example 2B, with the results shown in FIG. 3, discussed above.

D. Contents Mixing Assay

Since the $R_{18}$ fusion assay does not discriminate entirely between membrane apposition and bona fide membrane fusion, the conclusion that plasmenyl ethanolamine molecular species facilitate membrane fusion is further substantiated by quantitation of internal contents mixing.

To assess membrane fusion rates, the interior of PCFS and PC/PE SUVs (equimolar mixtures of PC/PE for both 16:0–18:1 plasmenyl ethanolamine and 16:0–18:1) were loaded with dipicolinic acid and $Tb^{3+}$, respectively, and the rates of mixing of internal contents were quantified on the basis of the increase in fluorescence intensity resulting from the formation of Tb/DPA complex, with the results shown in FIG. 4.

EXAMPLE 4

Preparation of GAPDH Isoform

A. Measurement of Glyceraldehyde 3-Phosphate Dehydrogenase Activity

The activity of GAPDH was measured spectrophotometrically utilizing modifications of the methods of Cori, \at al. (1948) and Steck, et al. (1973). Briefly, sample was added to a 1 cm path-length semi-micro cuvette containing 50 mM triethanolamine (pH 7–6), sodium arsenate (50 mM) (pH 8.8), 2.4 mM glutathione (reduced), 0.5 mM NAD, and water in a final volume of 990 \pl. After establishing a baseline (1 min), the reaction was initiated with 10 $\mu$l of 10 mM D-glyceraldehyde 3-phosphate (prepared according to Sigma product bulletin G-8007) and absorbance at 340 nm was measured for 5 minutes. Units of GAPDH activity represent the mass ($\mu$mol) of D-glyceraldehyde 3-phosphate converted per minute. The mass of NADH generated was calculated utilizing $\epsilon$=0.622.

B. Purification of the Membrane Fusion Protein from Rabbit Brain Cytosol

New Zealand White rabbits (typically, ten per preparation) were sacrificed by cervical dislocation and brains were harvested and placed in ice-cold homogenization buffer (30% w/v) consisting of 250 mM sucrose, 30 mM Tris•Cl, 10 mM EGTA, 2 mM EDTA, and 1 mM DTT, (pH 7.4, measured at 25° C.). Brains were homogenized using three 10 s pulses from a Brinkman PT 10/35 Polytron apparatus at incremental output settings of 4.5, 5, and 5.5. The homogenate was initially centrifuged at 10,000×g for 20 minutes and the resultant supernatant was centrifuged at 100,000×g for 60 minutes. The crude cytosol was twice dialyzed for 6 hours against 500 volumes of buffer A (50 mM Tris.Cl), 0.1 mM EGTA, 0.1 mM EDTA, and 1 mM DTT, pH 7.0 at 4° C.). The dialyzed cytosol was loaded onto a DE-52 column (2.6 cm×20 cm) previously equilibrated with buffer A at a flow rate of 2 ml/minute. Fractions from the DE-52 column were assayed for their ability to catalyze membrane fusion.

Activity was quantified in U/ml where U represents the nmol of lipid fused per second in an assay containing 200 $\mu$M lipid in a final volume of 100 $\lambda$. Fractions from the void volume containing fusion-catalyzing activity were pooled, filtered utilizing a Millipore GS 0.22 $\mu$m filter, and loaded onto a HiLoad SP Sepharose column (1.6 cm×10 cm, Pharmacia) previously equilibrated with 20 mM Tris.Cl, 0.1 mM EGTA, 0.1 mM EDTA, and 1 mM DTT, (pH 7.0 at 4° C.) (buffer B) at 3.0 ml/minute. After washing with 3 column volumes of buffer B, membrane fusion activity was eluted utilizing a nonlinear sodium chloride gradient from 0 to 0.5 M NaCl in buffer B. Active fractions from the HiLoad SP Sepharose column were pooled, diluted 3-fold with buffer B, and loaded onto a GTP-agarose column (Sigma, G-9768, Lot 7OH9545, 1 cm×5 cm) at a flow rate of 0.3 ml/minute. After washing the affinity matrix with 5 column volumes of buffer B, bound proteins were sequentially eluted with 5 mM GMP in buffer B, 3 mM GTP in buffer B and, finally, an additional 5 column volumes of buffer B alone. Membrane fusion activity was eluted with 20 mM tetrasodium tripolyphosphate and 10 mM NAD$^+$ in buffer B. Column eluents were assayed for GAPDH activity and membrane fusion activity.

GTP-agarose affinity eluents were further purified either by reverse phase HPLC (in preparation for protein sequencing) or by Mono Q chromatography. Anion exchange chromatography was accomplished utilizing a Mono Q column equipped for a Smart System FPLC (Pharmacia). Active fractions were pooled, diluted 10-fold into buffer C (20 mM Tris.Cl, 0.1 mM EGTA, 0.1 mM EDTA, and 1 mM DTT, pH 8.5 at 4° C.) and loaded onto a Mono Q PC 1.6/5 column previously equilibrate buffer C at a flow rate of 200 μl/minute. Fusion-catalyzing activity was eluted using a continuous gradient from 0 to 500 mM NaCl over 6 ml. Aliquots of column eluents were assayed for membrane fusion activity or subjected to [$^{125}$I]-Boulton-Hunter labeling previously described (Hazen, et al., 1990).

The GTP affinity column active fraction (0.1 ml) utilized for sequencing was diluted 1:1 with buffer containing 14% acetonitrile and 0.2% trifluoroacetic acid and loaded onto a C18 HPLC column (Vydac, 300 Å pore size, 4.6 mm×25 cm) pre-equilibrated with 10% mobile phase B at 500 μl/minute (mobile phase A: water containing 0.1% TFA; mobile phase B: 70% acetonitrile and 0.12% TFA). Proteins were eluted with a gradient of 10 to 70% mobile phase B over 50 minutes at a flow rate of 500 μl/minute. Homogeneity of the 38 kDa band eluting as the major uv absorbing peak from the RP-HPLC was verified by SDS-PAGE prior to submission for protein sequencing.

C. Two-Dimensional Electrophoresis

Two-dimensional electrophoresis was performed utilizing a Multiphor system (Pharmacia) with the first dimension isoelectric phast-gels cast utilizing Immobilines II in a 4% polyacrylamide matrix containing a pH gradient from pH 7.0 to 10.0 over 10 cm. Following polymerization, washing and drying of the gel, 3 mm strips were cut and reswelled in buffer containing 8 M urea, 1% NP-40 (Pierce SurfactAmps), 1 mM DTT, and 0.25% Pharmalyte 7–9 for 24 hours. Protein samples were diluted into buffer containing 10 M urea, 1% NP-40, 0.1% β-mercaptoethanol, and 0.25% Pharmalyte 7–9 and were concentrated utilizing Microcon-lo ultrafiltration units. First dimension gels were electrophoresed for 26 hours using a discontinuous voltage gradient (5 hours at 500 V, 18 hours at 2500 V and 2.5 hours at 3500 V). After equilibration of 1-D gels with SDS-PAGE buffer, samples were electrophoresed on either ExcelGel SDS 8–18% or ExcelGel SDS Homogeneous 12.5% gels (Pharmacia Biotech Inc.). Gels were subsequently either silver stained (BioRad Silver Stain Plus system) or transferred to PVDF paper for subsequent Western blotting.

EXAMPLE 5

Preparation of Anti-G6PDH of Monoclonal Antibodies

Four mice were initially injected with purified membrane fusion protein from the GTP-agarose column, and subsequent booster injections were made with rabbit muscle GAPDH. Hybridomas were formed from mouse spleen as described previously (Harlow & Lane, 1988) and supernatants were screened for anti-GAPDH antibodies by automated particle-concentration fluorescence immunoassays. Samples possessing activity after the initial screen were verified by Western blot analysis of rabbit brain cytosol. Hybridomas were used to generate ascites fluid by traditional methods (Harlow & Lane, 1988) and the resultant. IgG was purified from ascites fluid utilizing Protein-A agarose affinity chromatography.

EXAMPLE 6

Preparation of Tubulin Protein

A. Preparation of Tubulin

New Zealand rabbit brains were harvested after cervical dislocation and placed [30% (w/v)] in ice-cold homogenization buffer (250 mM sucrose, 30 mM Tris-Cl, 10 mM EGTA, 2 mM EDTA and 1 mM DTT, (pH 7.4, measured at 25° C.). Homogenization was performed utilizing three 10 sec pulses from a Brinkmann PT 10/35 polytron at incremental power settings of 4.5, 5, and 5.5. The homogenate was centrifuged at 10,000×g for 20 min and the supernatant was reserved. Subsequent centrifugation of the supernatant at 100,000×g for 60 min yielded crude cytosol, which was twice dialyzed against 500 volumes of buffer A (50 mM Tris-Cl, 0.1 mM EGTA, 0. 1 mM EDTA, and 1 mM DTT, pH 7.0 at 4° C.).

Dialyzed cytosol was loaded onto a DE-52 column (2.6 cm×20 cm) previously equilibrated with buffer A at a flow rate of 2 ml/min. Adsorbed proteins were eluted utilizing a 0–400 mM NaCl gradient in buffer A over 400 ml. The inhibitory potency of column eluents was assessed after appropriate dilution (as indicated in the figure legends) by quantifying the differences in percent of GAPDH isoform-catalyzed membrane fusion in the presence relative to the absence of diluted aliquots of column eluents. Fractions containing the highest levels of inhibitory activity were pooled, dialyzed against 100 volumes of buffer B (20 mM Tris-Cl, 0.1 mM EGTA, 0.1 mM EDTA and 1 mM DTT, (pH 7.0 at 4° C.)) and loaded onto a Mono Q column previously equilibrated with buffer B. Adsorbed proteins were eluted utilizing a nonlinear NaCl gradient (O Lo 600 mM NaCl in buffer B) as shown in the figure legends. To further exploit the resolving power of Mono Q chromatography, the most potent inhibitory fractions were pooled, dialyzed against buffer B, and rechromatographed on the Mono Q column utilizing a shallow gradient of NaCl in buffer B.

B. Purification of Tubulin by Assembly/Disassembly cycling

Tubulin was purified by assembly/disassembly of microtubules using the method of Shelanski, et al., (1979). Briefly, rabbit brain cytosol was prepared as described above and diluted (1:1, v/v) with buffer comprised of 8 M glycerol, 2 mM GTP, 200 mm NaMES, 1 mM $MgCl_2$, and 2 mM EGTA (pH 6.4). After incubation at 37° C. for 20 minutes (during which time microtubule assembly occurred), microtubules were pelleted by centrifugation at 100,000×g for 60 min at 25° C. The pellet was resuspended in ice-cold (4° C.) buffer (100 mM NaMES, 0.5 mM $MgCl_2$, and 1 mM EGTA (pH 6.4)) and dispersed using a Potter Elvehjem homogenizer and incubated at 4° C. for 20 min. After microtubule disassembly, the sample was centrifuged at 100,000×g and the supernatant collected. To the supernatant, an equal volume of buffer (8 M glycerol, 2 mM GTP, 200 mM NaMES, 1 MM $MgCl_2$, and 2 MM EGTA (pH 6.4)) was added. Microtubule formation was again accomplished by incubation at 37° C. for 20 minutes and the above sequence of centrifugation and disassembly was repeated.

After the second disassembly, tubulin was further purified from microtubule-associated proteins by Mono Q chromatography. The supernatant was filtered, dialyzed against buffer C (100 mM NaMES, 1 mM EGTA, and 0.5 mM $MgCl_2$ (pH 6.6)) and loaded onto a Mono Q column previously equilibrated with buffer C. Bound tubulin was eluted utilizing a nonlinear NaCl gradient in buffer C as indicated in the figures. Tubulin-containing column eluents were twice dialyzed against a 100-fold excess of buffer D (10 mM potassium phosphate (pH 7.0) containing 0. 3 mM $Cacl_2$) prior to loading onto an BioGel HPHT hydroxylapatite column (Bio Rad) (1×5 cm) previously equilibrated with buffer D. The column was developed utilizing a gradient of 10 mM potassium phosphate, 0.3 MM $CaCl_2$ to 350 mM potassium phosphate, 0.01 mM $CaCl_2$ in buffer D over a 30 ml volume.

C. Preparation of Tubulin-Sepharose Affinity Resin and Affinity Chromatography

Homogeneous tubulin (purified by the assembly/disassembly method followed by sequential Mono Q and HA chromatographies) was twice dialyzed against 100 volumes of buffer E (0.1 M NaHCO$_3$ with 0.5 M NaCl (pH 8.0)). The tubulin solution (0.1 mg/ml) was dialyzed against 100 volumes of buffer E for 15 h and was added, in equal volumes to a solution of activated CNBr-Sepharose (1 g/5 ml). After incubation for 24 h at 4° C., unreacted groups were blocked with 0.2 M glycine (pH=8.0) for 2 hours and the tubulin-sepharose matrix was washed with repetitive alternating washes of buffer E and buffer F (0.1 M acetate, 0.5 M NaCl, pH 4.5). After equilibration of the tubulin-Sepharose column (0.9×5 cm) with buffer B (20 mM Tris-Cl, 0.1 mM EGTA, 0.1 mM EDTA, and 1 mM DTT, (pH 7.0 at 4° C.) protein was loaded onto the column, washed with 10 column volumes of buffer B and bound proteins were eluted with a step gradient 0.5 M NaCl in buffer B.

Although the invention has been described with respect to particular formulations, compositions, and methods, it will be appreciated that various changes and modifications can be made without departing from the invention.

What is claimed is:

1. A lipid-vesicle composition in the form of a kit, said kit comprising
   a first population of lipid vesicles containing a first agent entrapped in said vesicles, said vesicles in the first population composed of (i) at least 10 mole percent of a plasmalogen phospholipid with a small-volume polar head group, (ii) a negatively charged phospholipid, and (iii) cholesterol or a cholesterol analog;
   a second population of lipid vesicles containing a second agent entrapped in said vesicles, said vesicles in the second population composed of a vesicle-forming lipid capable of fusion with the first-population vesicles; and
   a fusion protein effective to promote fusion between the vesicles in the two populations, said fusion protein selected from the group consisting of an isoform of glyceraldehyde-3-phosphate dehydrogenase, an N-ethylmaleimide-sensitive fusion protein, viral fusion proteins and fragments thereof which retain fusion activity;
   wherein said first and second populations, prior to use, are maintained in a condition that inhibits fusion until the two populations are brought into contact in the presence of said fusion protein.

2. The lipid vesicle composition of claim 1, wherein the first-population vesicles contain between 30–70 mole percent of the plasmalogen phospholipid.

3. The lipid vesicle composition of claim 1, wherein the small-volume polar head group on the plasmalogen phospholipid is selected from the group consisting of serine, ethanolamine and hydroxyl.

4. The lipid vesicle composition of claim 1, wherein the first-population vesicles contain between 3–15 mole percent of the negatively charged phospholipid.

5. The lipid vesicle composition of claim 1, wherein the first-population vesicles contain between 10–60 mole percent of cholesterol or cholesterol analog.

6. The lipid vesicle composition of claim 1, wherein the vesicles in the first population are composed of between 10–80 mole percent plasmenyl ethanolamine, 3–15 mole percent negatively charged phospholipid and 10–60 mole percent cholesterol.

7. The lipid vesicle composition of claim 1, wherein the first-population vesicles are composed of between 20–40 mole percent plasmenyl ethanolamine, 3–10 mole percent phosphatidylserine and 30–50 mole percent cholesterol.

8. The lipid vesicle composition of claim 1, wherein the first or second agent is selected from the group consisting of, peptides, proteins, oligonucleotides, nucleic acids, genes and gene fragments.

9. The lipid vesicle composition of claim 1, wherein the first or second agent is an antisense oligonucleotide.

10. The lipid vesicle composition of claim 1, wherein the lipid vesicles in either the first or second populations further comprise a surface ligand for cell-specific binding to target cells.

11. The lipid vesicle composition of claim 1, wherein the first population of lipid vesicles is composed of at least 10 mole percent of plasmenylethanolamine.

12. The lipid vesicle composition of claim 11, wherein the first population of lipid vesicles further comprises phosphatidylcholine and the second population of lipid vesicles is comprised of phosphatidylserine.

* * * * *